United States Patent [19]

Jarreau et al.

[11] Patent Number: 5,036,090

[45] Date of Patent: Jul. 30, 1991

[54] 3-ARYLOXAZOLIDINONE DERIVATIVES, PROCESS FOR THEIR PREPARATION AND THEIR USE IN THERAPY

[75] Inventors: Francois X. Jarreau, Versailles; Vincenzo Rovei, Rueil Malmaison; Jean-Jacques Koenig, Maisons Laffitte; Alain R. Schoffs, Paris, all of France

[73] Assignee: Delalande S.A., Courbevoie, France

[21] Appl. No.: 597,426

[22] Filed: Oct. 15, 1990

[30] Foreign Application Priority Data

Oct. 17, 1989 [FR] France ................ 89 13555

[51] Int. Cl.$^5$ .................. C07D 263/24; A61K 31/42
[52] U.S. Cl. ........................ 514/376; 548/232
[58] Field of Search ................ 548/232; 514/376

[56] References Cited

U.S. PATENT DOCUMENTS 4,338,451  7/1982  Doslert et al. .................. 548/232
4,517,197  5/1985  Ancher et al. ................... 548/232

Primary Examiner—Mary C. Lee
Assistant Examiner—Peter Davis
Attorney, Agent, or Firm—Zarley, McKee, Thomte, Voorhees & Sease

[57] ABSTRACT

The derivatives of the formula:

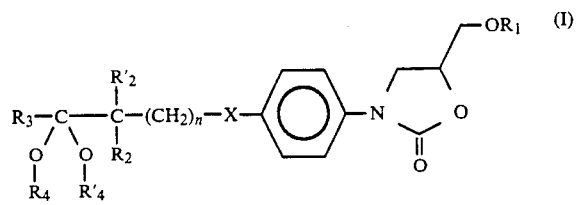

wherein:
$R_1$ is H or $C_1$-$C_4$ alkyl;
X is an oxygen atom, a methylene group or a —CH=CH— group;
n is 1 or 2 when X is an oxygen atom or a methylene group and is 0 or 1 when X is a —CH=CH— group;
$R_3$ is a $C_1$-$C_4$ alkyl, $C_3$-$C_7$ cycloalkyl, phenyl, benzyl, $CHF_2$, $CF_3$ or $CF_3CF_2$ group;
each of $R_2$ and $R'_2$ independently is a hydrogen atom or a $C_1$-$C_4$ alkyl, $C_4$-$C_7$ cycloalkyl, phenyl or benzyl group;
$R'_2$ and $R_3$ may further form together a —$(CH_2)_3$— or —$(CH_2)_4$— chain; and
each of $R_4$ and $R'_4$ independently is a $C_1$-$C_4$ alkyl group or $R_4$ and $R'_4$ form together either a —$(CH_2)_2$— or —$(CH_2)_3$— chain, a —$(CH_2)_2$— or —$(CH_2)_3$— chain substituted by one or two $C_1$-$C_4$ alkyl groups, or a —$(CH_2)_2$— chain substituted by one or two —$CH_2$—$NH_2$ groups or by one or two —$CH_2$—$NH_2$ groups N-substituted by one or two $C_1$-$C_4$ alkyl groups,
useful as drugs.

9 Claims, No Drawings

3-ARYLOXAZOLIDINONE DERIVATIVES, PROCESS FOR THEIR PREPARATION AND THEIR USE IN THERAPY

The present invention relates to new acetal derivatives of 3-aryl-2-oxazolidinone, to a process for their preparation and to their use in therapy.

More precisely, these derivatives correspond to the formula:

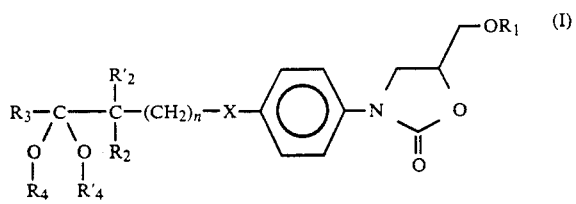

wherein:

$R_1$ is H or $C_1-C_4$ alkyl;

X is an oxygen atom, a methylene group or a —CH=CH— group;

n is 1 or 2 when X is an oxygen atom or a methylene group and is 0 or 1 when X is a —CH=CH— group;

$R_3$ is a $C_1-C_4$ alkyl, $C_3-C_7$ cycloaklyl, phenyl, benzyl, $CHF_2$, $CF_3$ or $CF_3CF_2$ group;

each of $R_2$ and $R'_2$ independently is a hydrogen atom or a $C_1-C_4$ alkyl, $C_4-C_7$ cycloalkyl, phenyl or benzyl group;

$R'_2$ and $R_3$ may further form together a —(CH$_2$)$_3$— or —(CH$_2$)$_4$—chain; and each of $R_4$ and $R'_4$ independently is a $C_1-C_4$ alkyl group or $R_4$ and $R'_4$ form together either a —(CH$_2$)$_2$—or —(CH$_2$)$_3$— chain, a —(CH$_2$)$_2$— or —(CH$_2$)$_3$—) chain substituted by one or two $C_1-C_4$ alkyl groups, or a —(CH$_2$)$_2$— chain substituted by one or two —CH$_2$—NH$_2$ groups or by one or two —CH$_2$—NH$_2$ groups N-substituted by one or two $C_1-C_4$ alkyl groups.

It should be moreover noted that the derivatives (I) include one or more asymmetric carbon atoms. They can therefore be under the form of diastereoisomers or enantiomers or under the cis- or trans-form or also under the form of a mixture of all theses forms, including the racemic forms. The present invention therefore encompasses the various forms so defined, with the exclusion of the racemates of formula (I) wherein $R_1 = CH_3$ and the

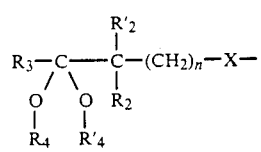

chaining has the meaning:

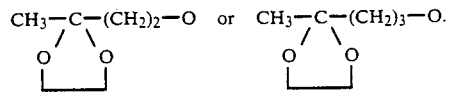

The invention also relates to the acid addition salts of the derivatives (I) which include a salifiable group. These salts can be formed with inorganic acids, such as hydrochloric, sulfuric, phosphoric acids, or with organic acids, such as fumaric, maleic, succinic, oxalic, citric or tartaric acids.

The above formula (I) particularly encompasses the derivatives for which:

$R_1 = H$ or $CH_3$;

$X = $ oxygen or $CH_2$;

n = 1 or 2;

$R_2 = R'_2 = H$;

$R_3 = C_1-C_4$ alkyl; and $R_4$ and $R'_4$ are $C_1-C_4$ alkyl or form together a —(CH$_2$)$_2$—chain, a —(CH$_2$)$_2$— chain substituted by two dimethylaminomethyl groups, a —(CH$_2$)$_3$— chain or a —(CH$_2$)$_3$— chain substituted by two CH$_3$ groups.

The derivatives for which:

$R_1 = CH_3$;

X = oxygen;

n = 1 or 2;

$R_2 = R'_2 = H$;

$R_3 = CH_3$ or $CF_3$; and $R_4$ and $R'_4$ are $CH_3$ or form together a —(CH$_2$)$_2$— chain;

the derivatives for which:

$R_1 = CH_3$;

X = methylene;

n = 1 or 2;

$R_2 = R'_2 = H$;

$R_3 = CH_3$ or $CF_3$; and $R_4$ and $R'_4$ are $CH_3$ or form together a —(CH$_2$)$_2$— chain; and the derivatives for which:

$R_1 = CH_3$;

X represents CH=CH;

n = 0 or 1;

$R_2 = R'_2 = H$;

$R_3 = CH_3$ or $CF_3$; and $R_4$ and $R'_4$ are $CH_3$ or form together a —(CH$_2$)$_2$— chain, are particularly mentioned.

The present invention moreover relates to the preparation processes of derivatives (I) and of their acid addition salts.

These processes are mainly based on two general synthetic routes.

The first one of these routes comprises creating an entity including the 2-oxazolidinone moiety (schemes 1 and 2), following by grafting on this entity the chain including the acetal residue (schemes 3 and 4).

Conversely, the second one of these routes comprises firstly creating the chain including the acetal residue (schemes 5 and 6), followed by creating and grafting on this acetal residue an entity including the 2-oxazolidinone moiety (schemes 7 and 8).

These eight schemes are represented below. Unless otherwise stated, the symbols $R_1$, X, n, $R_2$, $R'_2$, $R_3$, $R_4$ and $R'_4$ appearing in these schemes have the same meaning as in formula (I).

Scheme 1
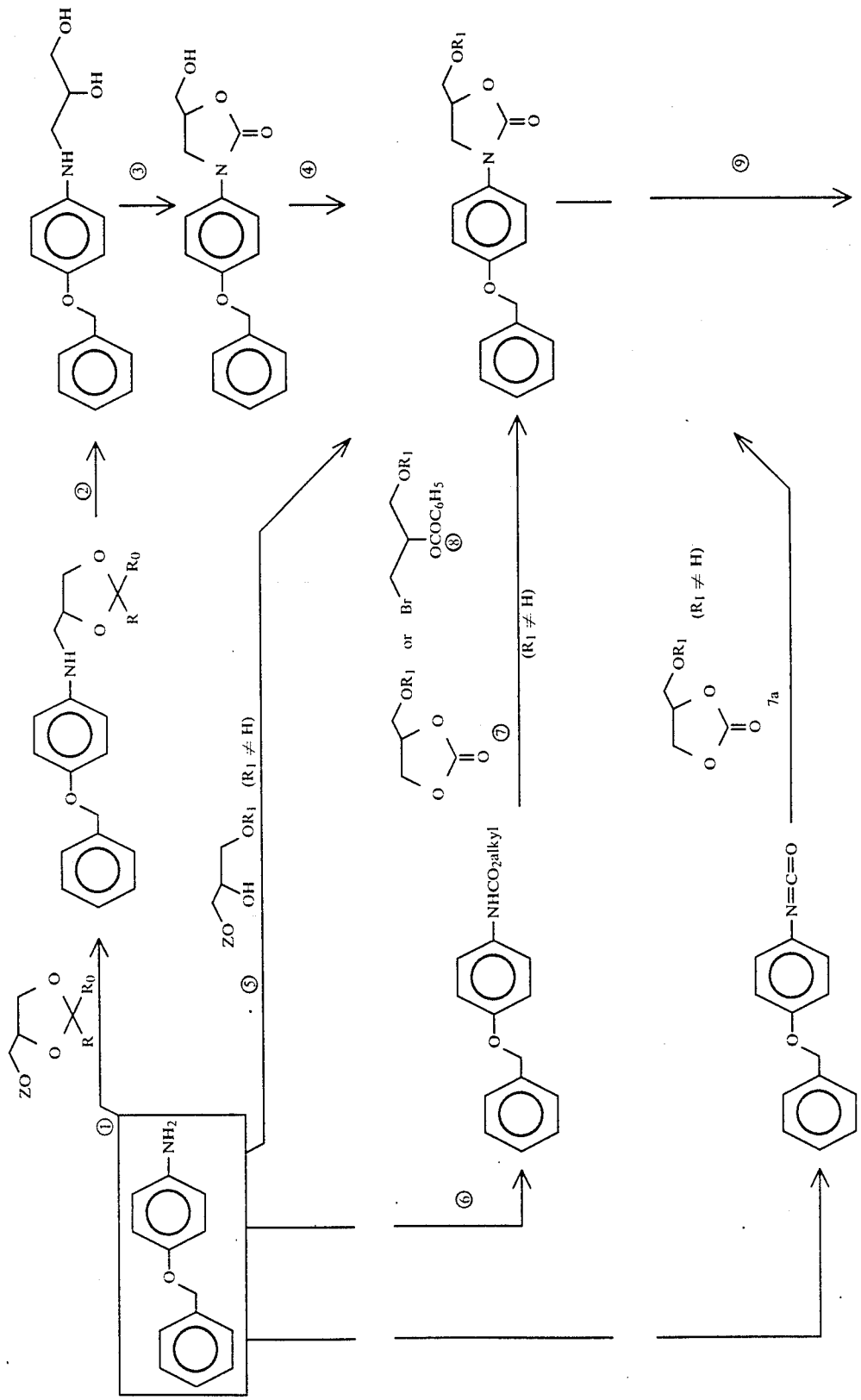

-continued
Scheme 1
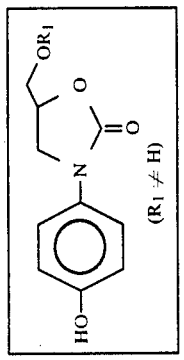
(R₁ ≠ H)
Z = Ms or Ts,
each of R and R₀ is C₁–C₃ alkyl or R and R₀ form together —(CH₂)₅—

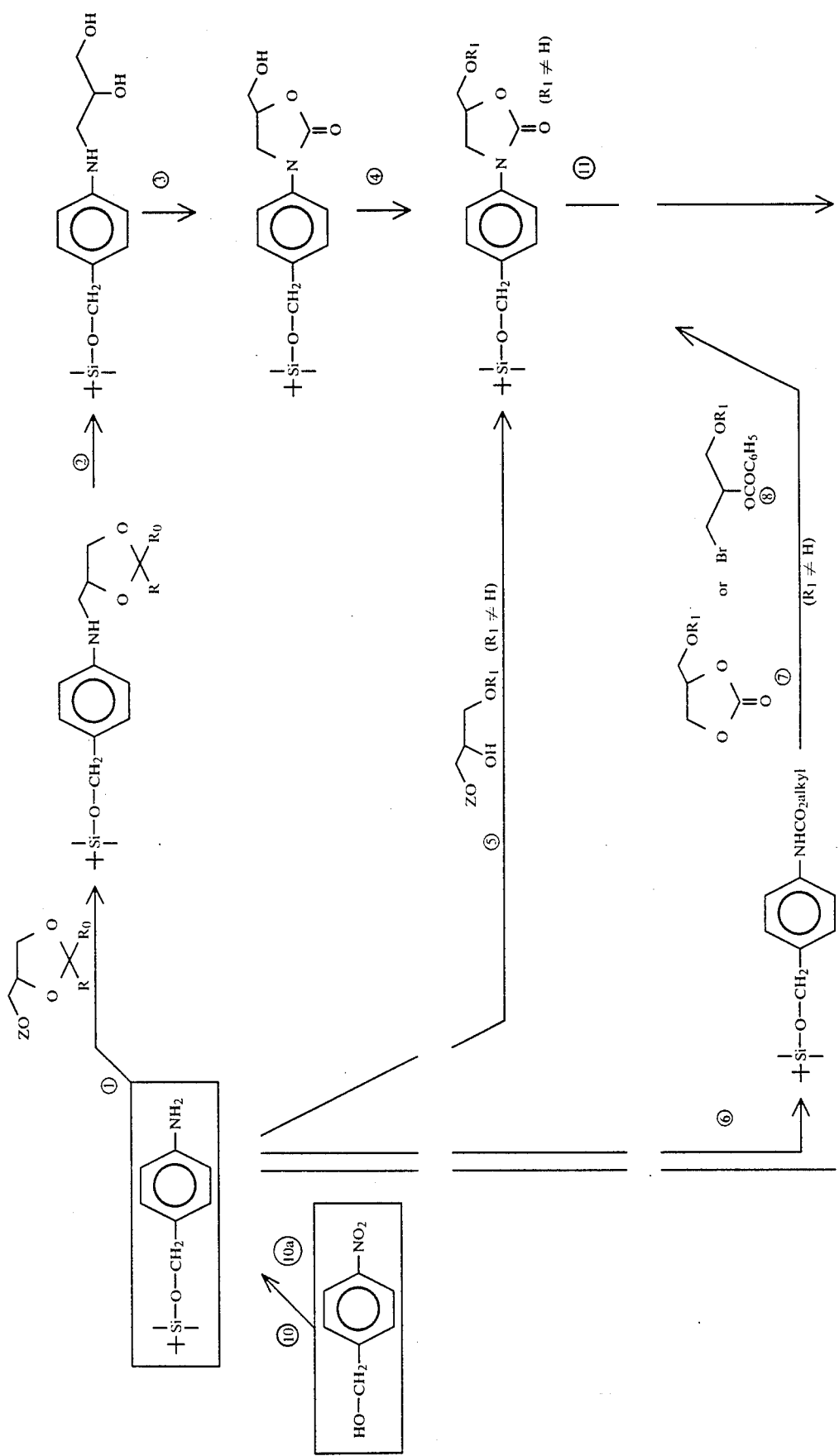
Scheme 2

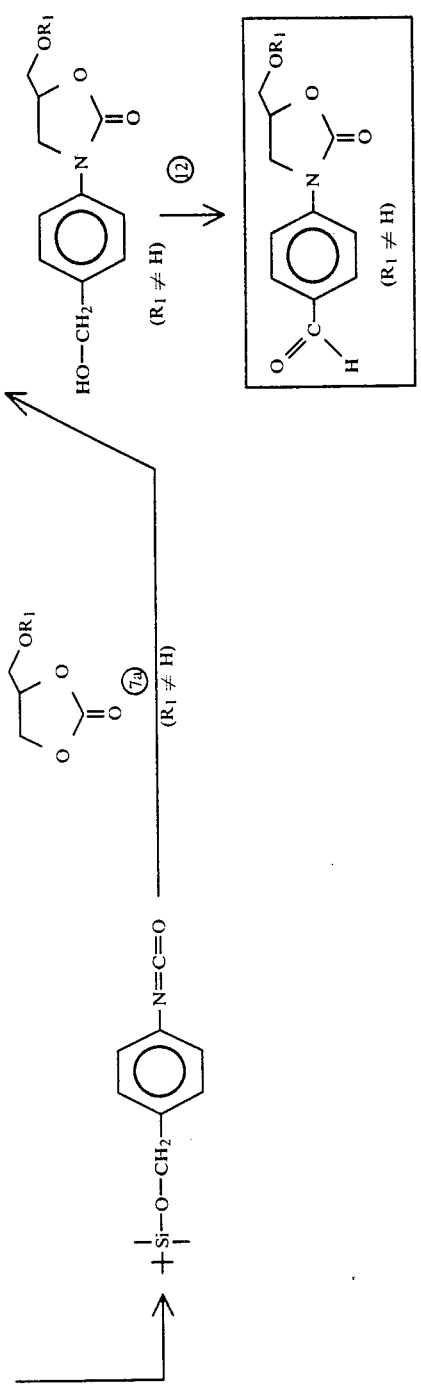
-continued
Scheme 2
Z = Ts or Ms
each of R and R₀ is C₁–C₃ alkyl or R and R₀ form together —(CH₂)₅—

Scheme 3
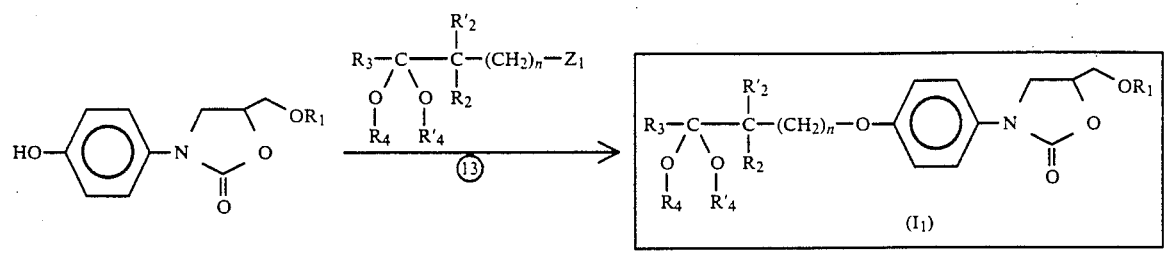
$R_2 = R'_2 = H$
$Z_1$ is OTs, OMs or halogen
Scheme 4
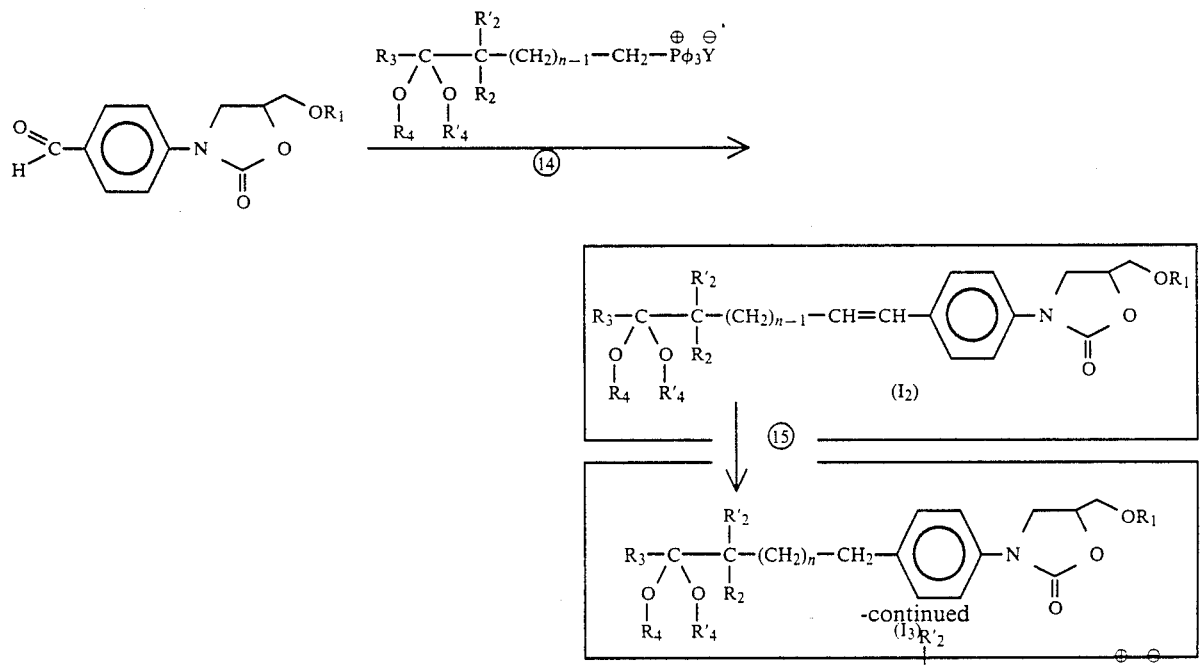
$Y$ = halogen
$R_1 \neq H$
Scheme 5
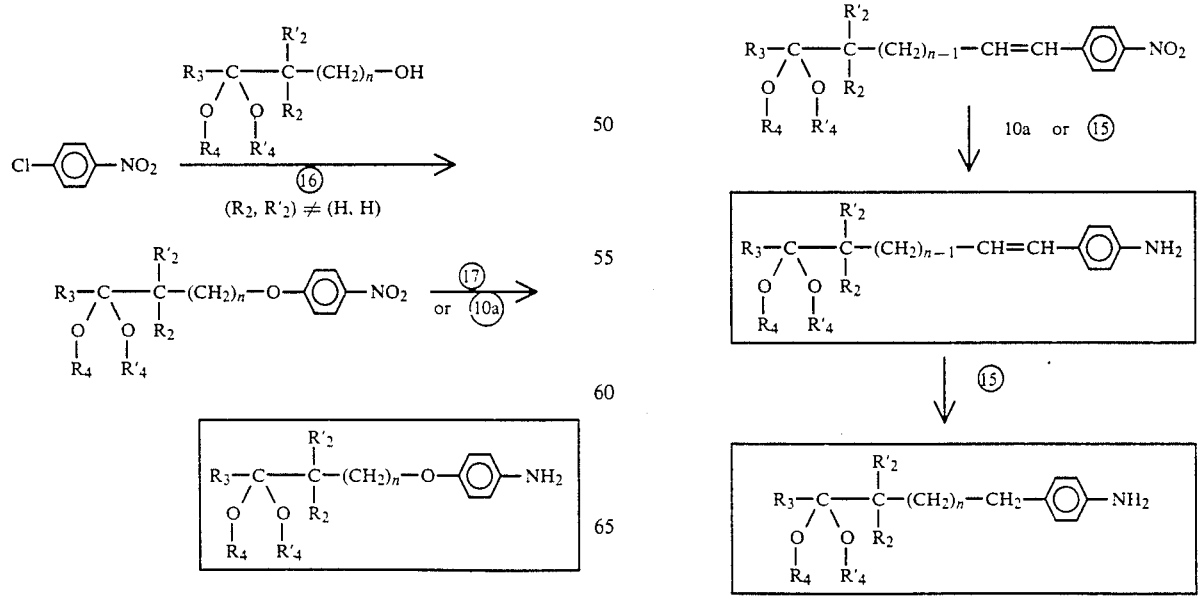
$(R_2, R'_2) \neq (H, H)$
Scheme 6
$Y$ = Halogen

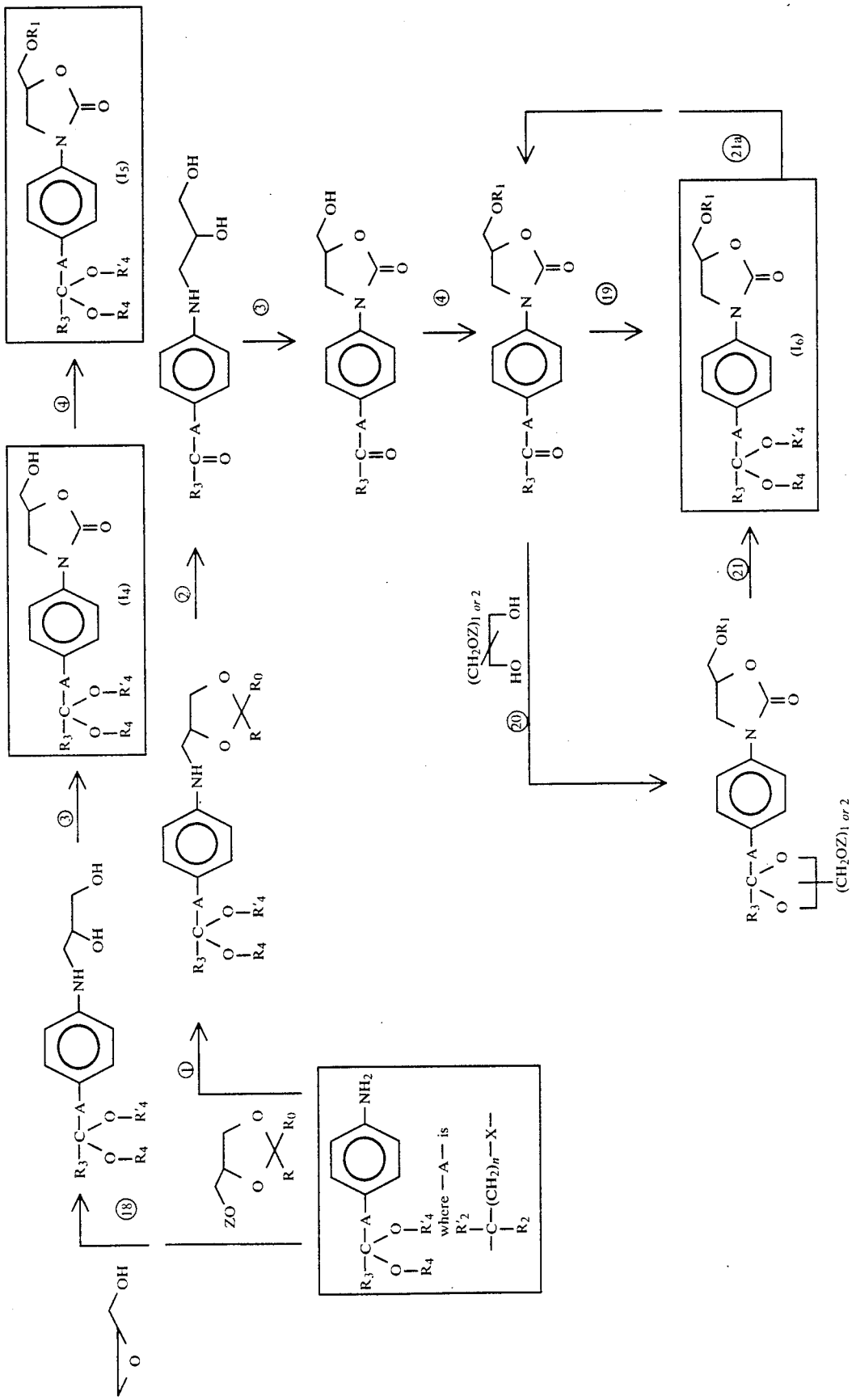
Scheme 7

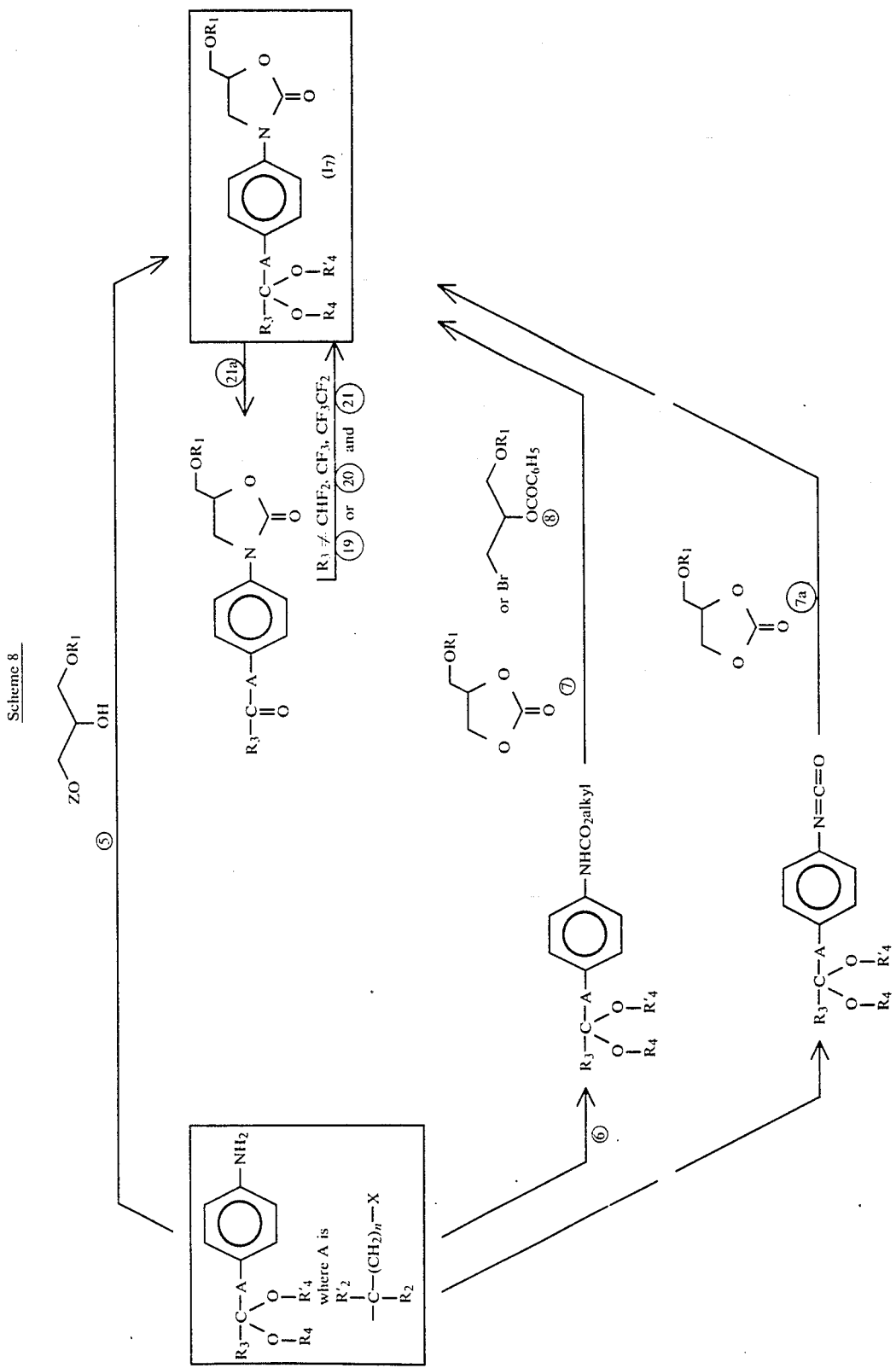

Moreover, the compounds of formulae:

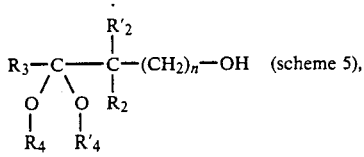
(scheme 5),

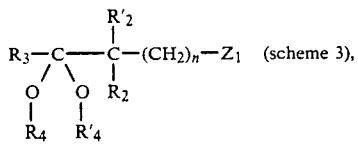
(scheme 3), and

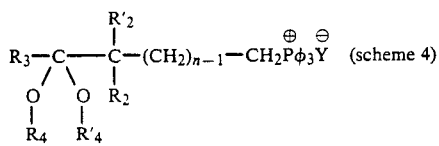
(scheme 4)

are obtained according to scheme 9 represented below.

Scheme 9

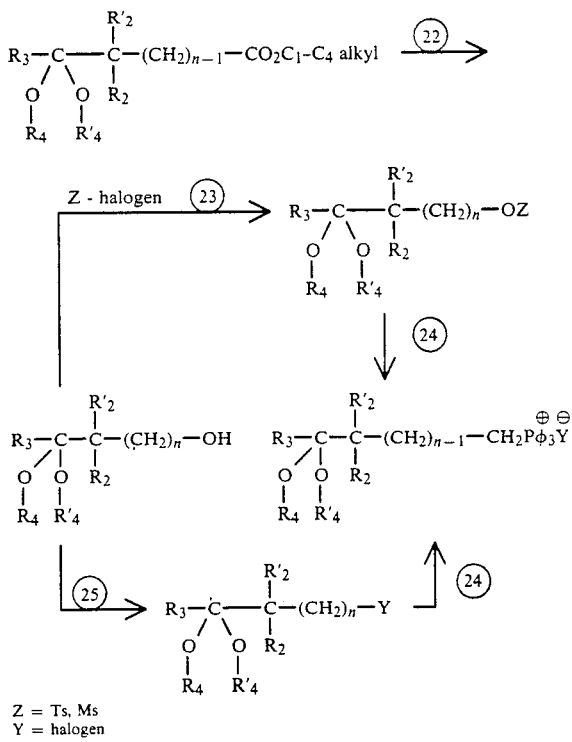

Z = Ts, Ms
Y = halogen

The ① to ㉕ number appearing in the above schemes have the following meanings:

① Condensation either in an anhydrous aprotic solvent like toluene, by heating, with or without a catalyst like hexadecyl tributyl phosphonium bromide or a quaternary ammonium halogenide such as benzyl triethylammonium bromide, or without solvent in the presence of triethylamine between 130-150° C.

② Hydrolysis with an aqueous acid, particularly 6N hydrochloric acid, in the presence of an organic solvent like methylethylcetone.

③ Condensation with a $C_1$-$C_4$ alkyl carbonate, particularly, diethyl carbonate, in an anhydrous solvent like toluene in the presence of an alkali metal alkoxide like sodium methoxide.

④ Alkylation with a $C_1$-$C_4$ alkyl halogenide (bromide or chloride) in phase transfer conditions, particularly sodium hydroxide-methylene chloride or toluene, in the presence of a quaternary ammonium like tetrabutylammonium bromide or hydrogen sulphate.

⑤ Condensation in the presence of phosgene and a base, particularly dimethylaniline, in an organic solvent like methylene chloride or dichloroethane; and then ring formation by heating in an organic solvent, particularly an alcoholic solvent like ethanol in the presence of a base, particularly potassium hydroxide.

⑥ Condensation with an alkyl chloroformate, like ethyl chloroformate, in the presence of a base, particularly, $NaHCO_3$, in a solvent mixture water-THF, at room temperature.

⑦ Condensation by heating (about 150° C.) in the presence of a base like $K_2CO_3$. The reaction retains the stereochemistry.

⑦a Condensation in toluene in the presence of LiBr and $nBu_3PO$.

⑧ Condensation in the presence of a base, particularly NaH, in an aprotic solvent like THF, at 55° C.-60° C.

⑨ Debenzylation in an alcoholic solvent like methanol or ethanol, in the presence of hydrogen and a catalyst, particularly 10% palladium-carbon, humidified or not.

⑩ O-silylation of the alcohol in an aprotic organic solvent like THF, in the presence of a base, particularly imidazole, and of terbutyldimethylchlorosilane.

⑩a Reduction of the nitro derivative with powdered iron in the presence of ammonium chloride.

⑪ Hydrolysis in an organic solvent, particularly THF, in the presence of a fluoride, particularly tetrabutylammonium fluoride.

⑫ Oxidation in the presence of oxalyl chloride, DMSO and a base, particularly triethylamine, in an aprotic organic solvent like methylene chloride.

⑬ O-alkylation in an anhydrous organic solvent like methylethylketone or DMF, and in the presence of a base, particularly, $K_2CO_3$, or
O-alkylation in an aprotic organic solvent like DMF and/or THF, and in the presence of an alkali metal hydride, like sodium hydride.

⑭ Condensation in the presence of a base, particularly $K_2CO_3$, and of formamide in an organic solvent, particularly dioxane, preferably under reflux, or
Condensation in the presence of LDA (lithium diisopropylamide) in a solvent mixture, particularly DMSO/THF.

⑮ Hydrogenation under atmospheric pressure of hydrogen in an organic solvent, particularly ethyl acetate, in the presence of a catalyst, like 10% palladium-carbon, humidified or not, or
Hydrogenation under hydrogen pressure, particularly, under 5 atm, in the presence of 10% palladium-carbon, humidified or not, in an alcoholic solvent, particularly ethanol, or
Hydrogenation under hydrogen pressure, particularly, under 9 atm, in the presence of 10% palladium-carbon, humidified or not, in an alcoholic solvent, particularly ethanol.

⑯ O-alkylation in an aprotic organic solvent, particularly DMF, in the presence of alkali metal hydride, particularly sodium hydride.

⑰ Hydrogenation under atmospheric pressure of hydrogen in an organic solvent, particularly ethyl acetate, in the presence of a catalyst like 10% palladium-carbon, humidified or not.

⑱ Condensation in an alcoholic solvent, like ethanol or isopropanol, at room temperature or by heating under reflux, in the absence or in the presence of a catalyst like cobalt chloride.

⑲ Acetalisation in the presence of aminopropyl grafted silica in the form of hydrochloride, with a $C_1$-$C_4$ alkanol, HO—$(CH_2)_2$—OH or HO—$(CH_2)_3$—OH, these diols being optionally substituted by one or two $C_1$-$C_4$ alkyl groups, in an aprotic solvent, particularly methylene chloride and with or without ethyl orthoformate, or Acetalisation with a $C_1$-$C_4$ alkanol, HO—$(CH_2)_2$—OH or HO—$(CH_2)_3$—OH, these diols being optionally substituted by one or two $C_1$-$C_4$ alkyl groups, under reflux in an aprotic organic solvent, particularly toluene, in the presence of paratoluene sulfonic acid, while removing the water formed.

⑳ The same operative conditions as in ⑲.

㉑ Condensation with ammonia, a ($C_1$-$C_4$ alkyl)amine or a di($C_1$-$C_4$ alkyl)amine, in an alcoholic solvent like methanol or ethanol, under heating.

㉑a Hydrolysis in the presence of silica and iron chloride hydrate in an organic solvent, particularly acetone or methylethylketone.

㉒ Reduction in an aprotic organic solvent like dimethoxyethane, in the presence of lithium borohydride, or in an organic solvent like THF in the presence of $LiAlH_4$.

㉓ Condensation in an organic solvent, particularly pyridine or $CH_2Cl_2$ in the presence of a base, particularly 4-dimethylamino-pyridine or $Et_3N$.

㉔ According to Helv. Chim. Acta 59, 755 (1976).

㉕ According to Can. J. Chem. 1968, 46, 86.

The following preparations are given by way of examples for illustrating the invention.

EXAMPLE 1

3-(4-Benzyloxyphenyl)-5(R)-methoxymethyl-2-oxazolidinone
(code number: 200404)

Step 1

3-(4-benzyloxyphenyl)aminopropane-1,2 -diol (R)
(code number 200418)

In an autoclave 1.5 kg of 4-benzyloxyaniline (7.564 mol), 2.014 kg of 1,4-dioxaspiro[4,5]decane2-methanol (S) mesylate (8.048 mol) and 1.88 l of triethylamine (13.5 mol) are added. The reagents are heated at 140° C. for 30 min. The reaction medium is then taken up in 7l of methylethylketone. The solution is washed with water and used for the subsequent step. To this solution, 1.2 l of 36% hydrochloric acid are added. The reaction medium is heated at 55° C. for 30 min. and cooled at 20° C. Soda lye is added until pH 9 is reached. The organic solution is washed with water and concentrated.

The product is obtained with a 90% yield; m.p.:102° C.; $[\alpha]_D^{20}= +12,7°$ (c=1, $CH_3OH$). This same product can be obtained by heating 4-benzyloxyaniline in ethanol in the presence of (R)-glycidol.

Step 2

3-(4-benzyloxyphenyl)-5(R)-methoxymethyl-2-oxazolidinone
(code number 200404)

To a suspension of 13 g (0.0475 mol) of compound 200418 in 100 ml of toluene, are added under reflux 6.2 ml (0.052 mol) of ethyl carbonate and 2 ml of 1M methanolic sodium methoxide. A distillation is carried out until the reflux reaches the boiling point of toluene. After cooling, $CH_2Cl_2$ is added and the organic solution is washed with water and dried over $Na_2SO_4$. After concentration, 14 g of 3-(4-benzyloxyphenyl)-5(R)-hydroxymethyl2-oxazolidinone (code number 220201) are obtained:

m.p.: 157° C.; $[\alpha]_D^{20}= -41°$ (c=1, $CH_2Cl_2$).

To 15 g (0.05 mol) of the previously obtained product 220201, are added 100 ml of toluene and 18.9 g of methyl sulphate, 1.8 g of tetrabutylammonium hydrogen sulphate, 10 ml of water and 10 g of NaOH. The reagents are heated for ½ h. The reaction medium is extracted with isopropyl ether and the aimed product is obtained with a 83% yield;

m.p.: 101° C.; $[\alpha]_D^{20}= -41,5°$ (c=1, $CH_2Cl_2$).

Using an identical procedure but starting from the suitable reagents, there were obtained 3-(4-benzyloxy-phenyl)-5(S)-methoxymethyl-2-oxazolidinone (code number 340190):

m.p.: 101° C.; $[\alpha]_D^{20}= +41,9°$ (c=1, $CH_2Cl_2$), as well as 3-(4-benzyloxyphenyl)-5(R)-ethoxymethyl-2-oxazolidinone (code number 230242):

m.p.: 78° C.; $[\alpha]_D^{20}= -35,9°$ (c=1, $CH_2Cl_2$);

IR (KBr) $\nu cm^{-1}$: 1750, 1735.

EXAMPLE 2

3-(4-hydroxyphenyl)-5(R)-methoxymethyl-2-oxazolidinone
(code number 200405)

To a solution of 13 g (0.047 mol) of the compound 200404 in 80 ml of ethanol and 40 ml of $CH_2Cl_2$ in the presence of 2.6g of 50% humidified 10% Pd/C, a hydrogen stream is passed through under normal pressure.

After completion of the reaction, the solution is filtered and concentrated. The aimed product is obtained with a 100% yield.

m.p.: 112° C.; $[\alpha]_D^{20}= -67°$ (c=1, $CH_3OH$);

IR (KBr) $\nu cm^{-1}$: 3260, 1730.

Using an identical process but starting from the corresponding reagent,, there are obtained the 3-(4-hydroxyphenyl)-5(S)-methoxymethyl-2-oxazolidinone (code number 200717):

m.p.: 114° C.; $[\alpha]_D^{20}= +66°$ (c=1, $CH_3OH$), and the 3-(4-hydroxyphenyl)-5(R)-ethoxymethyl-2-oxazolidinone (code number 230243):

m.p.: 92° C.; $[\alpha]_D^{20}= -58,9°$ (c=1, $CH_3OH$).

EXAMPLE 3

3-[4-[2-(2-methyl-1,3-dioxolane-2-yl)ethoxy]phenyl]-5(R)-methoxymethyl-2-oxazolidinone (code number 370296)

To a solution of 50 ml of DMF, are added 3 g (0.076 mol) of 60% NaH and, over 15 min., 16 g (0.076 mol) of compound 200405 dissolved in 75 ml of DMF. Then, while keeping temperature at 20° C., 0.0836 mol of 2-(2-mesyloxy-ethyl)-2-methyl-dioxolane dissolved in 25 ml of DMF. The reaction medium is left at room temperature for 24 hours and poured on iced water. The aqueous phase is extracted with $CH_2Cl_2$ and the organic phase is dried over magnesium sulphate. The product is obtained after purification on silica column (eluent: Heptane: 40; Ethyl acetate: 60) with a 44% yield;

m.p.=48° C.; $[\alpha]_D^{20}= -32,8°$ (c=1, $CH_2Cl_2$);

¹H NMR (CDCl₃) δ ppm: 1.4 (3H); 2.2 (2H); 3.4 (3H); 3.6 (2H);
3.9 (4H); 3.7–4.3 (4H);
4.7 (1H); 6.8 (2H); 7.4 (2H);
IR (KBr) ν cm⁻¹: 1740.
¹³C NMR Cq: 155.6; 154.4; 131.5; 108.7;
CH: 120.2; 114.9; 71.2;
CH₂: 72.7; 64.6; 64.3; 47.5; 38.2;
CH₃: 59.6; 24.4.
In the same manner, there were obtained
3-[4-[3-(2-methyl-1,3-dioxolane-2-yl)propoxy]phenyl]-5(R)-methoxymethyl-2-oxazolidinone (code number 370506):
¹H NMR (CDCl₃) δ ppm: 1.35 (3H); 1.8 (4H);
3.4 (3H); 3.6 (2H);
3.7–4.2 (4H); 3.9 (4H);
4.7 (1H); 6.8 (2H);
7.4 (2H);
IR (KBr) ν cm⁻¹: 1750.
m.p.=67° C.;
3-[4-[2-(2,5,5-trimethyl-1,3-dioxane-2-yl)ethoxy]-phenyl]-5(R)-methoxymethyl-2-oxazolidinone (code number 370445):
¹H NMR (CDCl₃) δ ppm: 0.8(3H); 1(3H);
1.4 (3H); 2.2 (2H);
3.4 (3H); 3.5 (4H);
3.6 (2H); 3,7–4.3 (4H);
4.7 (1H); 6.8 (2H);
7 4 (2H);
IR (microcell) ν cm⁻¹: 1750;
[α]$_D^{20}$= −32,2°(c=1, CH₂Cl₂);
3-[4-[2-(2-methyl-1,3-dioxolane-2-yl)ethoxy]phenyl]-5(R)-hydroxymethyl-2-oxazolidinone (code number 230046):
¹H NMR (CDCl₃) δ ppm: 1.4 (3H); 2.15 (2H);
3 (1 exch. H); 3.9 (4H);
3.6–4.2 (6H); 4.6 (1H);
6.2 (2H); 7.4 (2H);
IR (KBr) ν cm⁻¹: 3480, 1710.
[α]$_D^{20}$= −40.2°(c=1, CH₂Cl₂);
m.p.=132° C.
yield=96% (from 3-[4-hydroxyphenyl]-5(R)-hydroxy-methyl-2-oxazolidinone;
3-[4-(dioxaspiro[4,4]nonane[1,4]-6-yl-methoxy)phenyl]-5(R)-methoxymethyl-2-oxazolidinone (code number 230204)
[α]$_D^{20}$= −44.8°(c=1, CH₃OH);
¹H NMR (CDCl₃) δ ppm 1.4–2.6 (7H); 3.4 (3H);
3.6 (2H); 3.8–4.2 (8H);
4.7 (1H); 6.9 (2H);
7.4 (2H);
Oily product.

EXAMPLE 4

3-[4-(3,3-dimethoxybutoxy)phenyl]-5(R)-methoxymethyl-2-oxazolidinone (code number 370297)
To 200 ml of anhydrous methanol, are added 10 g of the compound having code number 370268 (Example 6) and 1 g of aminopropyl silica as hydrochloride. The mixture is left under stirring for 72 h. After filtration and concentration, the product is obtained by silica column chromatography (eluent: Ethyl acetate: 60; Heptane: 40) with a 88% yield as an oil.
[α]$_D^{20}$= −36.7°(c=1, CH₂Cl₂).
IR (KBr ν cm⁻¹: 1750;
¹H NMR (CDCl₃) δ ppm: 1.35 (3H); 2.1 (2H); 3.2 (6H);
3.4 (3H); 3.6 (2H);
3.8–4.2 (2H); 4 (2H); 4.7 (1H);
6.9 (2H); 7.4 (2H).
¹³C NMR (CDCl₃): Cq: 155.6; 100.4;
CH: 120.2; 115; 71.2;
CH₂: 72.7; 64.6; 47.6; 36.1;
CH₃: 59.6; 48.1; 21.7.
In the same manner, there was obtained
3-[4-(3,3-dimethoxybutoxy)phenyl]-5-methoxymethyl-2-oxazolidinone (code number 370339):
¹H NMR (CDCl₃) δ ppm: 1.35 (3H); 2.1 (2H);
3 2 (6H); 3.4 (3H);
3.6 (2H); 3.7–4.2 (2H);
4 (2H); 4.7 (1H);
6.3 (2H); 7.4 (2H);
IR (KBr) ν cm⁻¹: 1750;
Oil.

EXAMPLE 5

3-[4-[3-[4(S),5(S)-bis (N,N-dimethylaminomethyl)-2-methyl-1, 3-dioxolane-2-yl]propoxy]phenyl]-5(R)-methoxymethyl-2-oxazolidinone: I₆ (code number 230085)

Step 1

3-[4-[3-[4(S),5(S)-bis(tosyloxymethyl)-2-methyl1,3-dioxolane-2-yl]propoxy]phenyl]-5(R)-methoxy-methyl-2-oxazolidinone (code number 230146)
To a solution of 4.6 g (0.0149 mol) of compound 370507 (Example 6) in 225 ml of toluene, are added 0.9 g of paratoluene sulphonic acid hydrate and 6.4 g (0.0149 mol) of 1,4-ditosyloxy-(4S,5S)-butane-2,3-diol and the mixture is heated under reflux for 6h while removing the water. After concentration, the residue is taken up in CH₂Cl₂ and the solution is washed with NaHCO₃ saturated water, and concentrated. The product is obtained after flash chromatography (silica, eluent: CH₂Cl₂: 99; MeOH: 1) with a 87% yield.
m.p.=104° C.

Step 2

3-[4-[3-[4(S),5(S)-bis(N,N-dimethylaminomethyl)-2-methyl-1, 3-dioxolane-2-yl]propoxy]phenyl]-5(R)-methoxymethyl 2-oxazolidinone: I₆ (code number 230085)
To a solution of 7.4 g (0.0105 mol) of compound 230146 in 300 ml of methanol cooled at 0° C., are added 14 ml (0.209 mol) of dimethylamine in an autoclave and the mixture is heated at 90° C. for 4 h. After concentration, the residue is taken up in water (50 ml) and 5 ml of concentrated aqueous ammonia are added. The aqueous solution is extracted with CH₂Cl₂. The organic phase is dried over Na₂SO< and concentrated. The product is purified by flash chromatography (silica, eluent: CH₂Cl₂: 90; MeOH: 9; NH₄OH: 1), oil.
¹H NMR (CDCl₃) δ ppm: 1.4 (3H); 1.8 (4H); 2.3 (12H);
2 4 (4H); 3.4 (3H); 3.6 (2H);
3.6–4.2 (6H); 4.7 (1H);
6.8 (2H); 7.4 (2H);
IR (microcell) ν cm⁻¹: 1750.
[α]$_D^{20}$= −55.5°(c=1, MeOH).

EXAMPLE 6

3-[4-(3-oxobutoxy)phenyl]-5(R)-methoxymethyl-2-oxazolidinone
(code number 370268)
To a solution of 294 g (0.871 mol) of compound 370296 (Example 3) in 2,5 1 of acetone, are added 600 g of (FeCl$_3$, 6H$_2$O, SiO$_2$)$_n$ over 10 min. After 4 hours of stirring, the reaction medium is filtered and dried over Na$_2$SO$_4$ and concentrated. The product is obtained with a 74.1% yield.

m.p.=49° C.; $[\alpha]_D^{20}$= −42.6°(c=1, CH$_2$Cl$_2$);

$^1$H NMR (CDCl$_3$) δ ppm: 2.2 (3H); 2.85 (2H); 3.4 (3H);
3.6 (2H); 3.8–4.4 (4H);
4.7 (1H); 6.8 (2H); 7.4 (2H);
IR (KBr) ν cm$^{-1}$: 1750, 1710.

In the same manner, there were obtained

3-[4-(4-oxopentoxy)phenyl]-5(R)-methoxymethyl-2-oxazolidinone (code number 370507)

$^1$H NMR (CDCl$_3$) δ ppm : 2 (2H); 2.15 (3H);
2.6 (2H); 3.4 (3H);
3.6 (2H); 3.9 (4H);
4.65 (1H); 6.8 (2H);
7.4 (2H);
IR (KBr) ν cm$^{-1}$: 1760, 1710;
$[\alpha]_D^{20}$= −40.3°(c=1, CH$_2$Cl$_2$);
m.p.=70° C.

3-[4-(3-oxobutoxy)phenyl]-5(R)-hydroxymethyl-2-oxazolidinone (code number 230047)

$^1$H NMR (CDC$_3$) δ ppm : 2.2 (3H); 2.9 (2H);
3.3–4.3 (4H); 4.2 (2H);
4.7 (1H); 5.2 (1 exch. H);
6.9 (2H); 7.5 (2H);
IR (KBr) ν cm$^{-1}$: 3450, 1720;
$[\alpha]_D^{20}$= −49.4°)c=1, CH$_3$OH);
m.p.=126° C.

EXAMPLE 7

3-[4-(3-oxo-2,2-dimethylbutoxy)phenyl]-5(R)-hydroxymethyl-2-oxazolidinone
(code number 230109)

Step 1

2,2-Dimethyl-2-(2-methyl-1.3-dioxolane-2-yl)ethanol
(code number 230103)

A solution of 35 g (0.073 mol) of 3,3-dimethyl-3-(2-methyl-1,3-dioxolane-2-yl) propionic acid ethyl ester in 50 ml of THF is added at 0° C. to a suspension of 7.23 g (0.19 mol) of LiAlH$_4$ in 300 ml of THF over 15 min. Then the reaction medium is hydrolyzed with 20 ml of water. After filtration and concentration, the product is obtained with a 92% yield.

IR (KBr) ν cm$^{-1}$: 3450, 2980, 2880;
$^1$H NMR (CDCl$_3$) δ ppm: 1 (6H); 1.2 (3H); 3.5 (2H); 4 (4H).

Step 2

2-methyl-2-[2-(4-nitrophenoxy)-1,1-dimethylethyl]-1,3-dioxolane
(code number 230105)

To a solution of 1.6 g (0.01 mol) of compound 230103 in 13 ml of DMF, are added 0.48 g (0.01 mol) of 50% NaH. After 15 min of stirring, a solution of 1.32 g (0.0084 mol) of parachloronitrobenzene is added and agitated at room temperature for 30 min.

The reaction medium is poured on water and extracted with isopropyl ether. The organic phases are washed with NaCl saturated water, dried over Na$_2$SO$_4$ and concentrated. The product is purified by flash chromatography (silica, eluent: heptane: 80; ethyl acetate: 20). Yield: 68% ; oil;

$^1$H NMR (CDCl$_3$) ν ppm: 1.1 (6H); 1.3 (3H); 4 (6H); 6.9 (2H); 8.1 (1H).

Step 3

2-methyl-2-[2-(4-aminophenoxy)-1,1-dimethylethyl]-1,3-dioxolane
(code number 230106)

To a solution of 18.4 g (65.4×10$^{-3}$ mol) of compound 230105 in 180 ml of ethanol in the presence of 50% humidified 10% Pd/C, a hydrogen stream is passed through under normal pressure for 3 h 30. After filtration and concentration, the product is purified by flash chromatography (silica, eluent: ethyl acetate: 30; heptane: 70).

$^1$H NMR (CDCl$_3$) δ ppm: 1.05 (6H); 1.3 (3H);
3 3 (2exch. H); 3.7 (2H);
3.9 (4H); 6.7 (4H).
IR (microcell) ν cm$^{-1}$: 3460, 3450.

Step 4

N-[4-[2-(2-methyl-1,3-dioxolane-2-yl)-1,1-dimethylethoxy] phenyl]-1,4-dioxaspiro[4,5]decane-2(R)-methanamine (code number 230107)

8.8 g (0.035 mol) of 230106 and 5.4 g (0.054 mol) of 1,4-dioxaspiro[4,5]decane-2-methanol (S) mesylate in triethylamine are heated in a bomb at 130° C.–140° C. for 2 h. After cooling, the reactio mixture is taken up in ethyl acetate. The organic phase is washed with NaCl saturated water and concentrated. The product is obtained after chromatography (silica, eluent: heptane 80 - ethyl acetate 20). Yield: 63%.

$^1$H NMR (CDCl$_3$) δ ppm: 1.1 (6H); 1.35 (3H);
1 6 (10H); 3.2 (2H);
3.6–4.5 (10 H of which 1 exch.);
6.65 (4H).
IR (microcell) ν cm$^{-1}$: 3400.
$[\alpha]_D^{20}$= −1.2°(c=1, MeOH).

Step 5

3-[4-(3-oxo-2,2-dimethylbutoxy)phenyl]amino-propane-1,2-diol (R) (code number 230108

To a solution of 0.7 g (1.7 10$^{-3}$ mol) of compound 230107 in 3.5 ml of THF, are dropwise added 3.5 ml of 6N hydrochloric acid. After 1h, the reaction medium is poured on water and extracted with ethyl acetate. The organic phase is washed with water. dried over Na$_2$SO$_4$ and concentrated. 80% yield IR (microcell) ν cm$^{-1}$: 3400, 1710.

Step 6

3-[4-(3-oxo-2,2-dimethylbutoxy)phenyl]-5(R)-hydroxymethyl-2-oxazolidinone
(code number 230109)

A solution of 3.9 g (0.0139 mol) of compound 230108 in 50 ml of toluene is heated under reflux and 1.88 g (0.0159 mol) of diethyl carbonate are added at 90° C., and then gradually 0.32 ml of a 4.3 mol/liter sodium methoxide solution.

After having distilled the alcohol, the reaction mixture is concentrated, the residue is taken up in ethyl acetate. The organic phase is washed with water, dried and concentrated. The product is obtained after column chromatography (silica, eluent: CH$_2$Cl$_2$);

m.p.=109° C.;
$[\alpha]_D^{20}$= −44.4°(c=1, MeOH);
$^1$H NMR (CDCl$_3$) ν ppm: 1.25 (6H); 2.2 (3H); 3.9 (6H);
4.7 (1H); 6.9 (2H); 7.4 (2H);
IR (KBr) ν cm$^{-1}$: 3450, 1745–1725.

EXAMPLE 8

3-[4-(3-oxo-2,2-dimethylbutoxy)phenyl]5(R)-methoxymethyl 2-oxazolidinone
(code number 230073)

To a suspension of 2.9 g (9.44 mmol) of compound 230109 in 40 ml of toluene and 40 ml of 50% NaOH, are added 0.3 g of tetrabutylammonium bromide and 2.7 ml (28.3 mmol) of methyl sulphate. After 30 min., the reaction medium is poured on water and extracted with ethyl acetate. The organic phase is washed with NaCl saturated water, dried and concentrated. After chromatography (silica, eluent: ethyl acetate 50; heptane 50), 2.2 g of product are obtained;

m.p.=75° C.; $[\alpha]_D^{20}=-52°(c=1, MeOH)$
hu 1H NMR (CDCl$_3$) δ ppm: 1.25 (6H); 2.2 (3H); 3.6 (2H);
3.7–4.2 (2H); 3.9 (2H);
4.65 (1H); 6.8 (2H); 7.4 (2H).
$^{13}$C NMR (CDCl$_3$) δ ppm: Cq: 211.9; 155.8; 154.9; 132; 48.4;
CH: 120.3; 115.1; 71.3;
CH$_2$: 74.9; 72.8; 47.8;
CH$_3$: 25.8; 22;
IR (KBr) ν cm$^{-1}$; 1735, 1715.

EXAMPLE 9

3-[4-(4-oxopentyl)phenyl]-5(R)-hydroxymethyl-oxazolidinone (code number 230116)

Step 1

2-(p-nitrocinnamyl)-2-methyl-1,3-dioxolane (code number 230111)

To 62.8 mmol of LDA in 226.4 ml of THF, is added dropwise at 0° C. a solution of 28.8 g (62.2 mmol) of (2-methyl-dioxolane-2-yl-2-ethyl)triphenylphosphonium bromide in 60 ml of DMSO. After 1 h at 0° C., 7.8 g (51.6 mmol) of p-nitrobenzaldehyde dissolved in 40 ml of THF are added. The reaction medium is hydrolyzed with a NH$_4$Cl saturated solution and is extracted with ethyl ether. The organic phase is dried over Na$_2$SO$_4$ and concentrated. After purification by flash chromatography (silica, eluent: heptane: 70; ethyl acetate: 30), the product is obtained with a 48% yield.

$^1$H NMR (CDCl$_3$) δ ppm: 1.3 (3H); 2.6 (2H); 4 (4H); 5.7–6.5 (2H); 7.4 (2H);
8.1 (2H).

Step 2

2-(4-aminocinnamyl)-2-methyl-1,3-dioxolane (code number 230112)

To a solution of 8 g (32 mmol) of compound 230111 in 100 ml of ethanol in the presence of 0.8 g of 10% Pd/C in an autoclave, a hydrogen stream is passed through under 5 atm for 4 h. After filtration, concentration, purification by flash chromatography (silica, eluent: heptane: 50; ethyl acetate: 50), the product is obtained with a 89% yield.

m.p.: <50° C.;
$^1$H NMR (CDCl$_3$) δ ppm: 1.35 (3H); 2.4–2.8 (2H);
3.6 (2 exch. H); 4 (4H);
5.5–6.3 (2H); 6.6 (2H);
7.2 (2H);
IR (microcell) ν cm$^{-1}$: 3460, 3440.

Step 3

2-[3-(4-aminophenyl)propyl]-2-methyl-1,3-dioxolane (code number 230113)

A solution of 15.4 g (70.23 mmol) of compound 230112 in 100 ml of ethanol in the presence of 1.5 g of 10% Pd/C is charged in an autoclave; a hydrogen stream is passed through under 9 atm for 1 h at 50° C. After filtration and concentration, 15.5 g of the aimed product (liquid) are obtained.

$^1$H NMR (CDCl$_3$) δ ppm: 1.25 (3H); 1.6 (4H);
2.45 (2H); 3.5 (2 exch. H);
3.85 (4H); 6.55 (2H); 6.9 (2H).
IR (microcell) ν cm$^{-1}$): 3460, 3350.

Step 4

[4-[3-(2-methyl-1,3-dioxolane-2-yl)propyl]phenyl]1,4-dioxaspiro[4,5]decane-2(R)-meth anamine (code number 230114)

To a mixture of 1 g (4,5 mmol) of compound 230113 and 1.62 g (4.97 mmol) of 1,4-dioxaspiro[4.5]decane-2-methanol (S) tosylate, is added 0.73 g (1 ml, 7.23 mmol) of triethylamine and the mixture is heated at 140° C. for 5 h. The reaction medium is taken up in water and extracted with ethyl acetate. The organic phase is washed with salted water, and then dried over Na$_2$SO$_4$. The product as a liquid is obtained with a 59% yield after flash chromatography (silica, eluent: heptane: 40; ethyl acetate: 60).

$^1$H NMR (CDCl$_3$) δ ppm: 1.2 (3H); 1.5 (10H); 1.6 (4H);
2.4 (3H); 3.15 (3H); 3.8 (4H);
3.6–4.5 (3H).
IR (microcell) ν cm$^{-1}$: 3400;
$[\alpha]_D^{20}=-2.9°(c=1, MeOH)$.

Step 5

[4-(4-oxopentyl)phenyl]aminopropane-1,2-diol (R) (code number 230115)

This compound was obtained according to the same procedure as that of Step 5 of Example 7

$^1$H NMR (CDCl$_3$) ν ppm: 1.8 (2H); 2 (3H); 2.4 (4H);
2.7–3.3 (3H); 3.1 (3H);
3.6 (2H); 3.3 (1H); 6.5 (2H);
6.9 (2H).

Step 6

3-[4-(4-oxopentyl)phenyl]-5(R)-hydroxymethyl-oxazolidinone (code number 230116)

This compound was obtained according to the same procedure as that of the Step 6 of Example 7:

m.p.=110° C.;
$[\alpha]_D^{20}=-50.7°(c=1, MeOH)$;
$^1$H NMR (CDCl$_3$) δ ppm: 1.8 (2H); 2.05 (3H);
2.2–2.7 (4H); 2.75 (1H);
3.65–4.10 (2H); 4.65 (1H);
7.1 (2H); 7.4 (2H);
IR (KBr) ν cm$^{-1}$: 3460, 1720.

Example 10

3-[4-(4-oxopentyl)phenyl]-5(R)-methoxymethyl2-oxazolidinone (code number 230083)

was obtained with a 100% yield according to the same procedure as that of Example 8:

m.p.:<50° C.;
$[\alpha]_D^{20}=-56.9°(c=1, MeOH)$;
$^1$H NMR (CDCl$_3$) δ ppm 1.9 (2H); 2.1 (3H); 2.45 (4H);
3.4 (3H); 3.6 (2H); 3.9 (2H);
4.7 (1H); 7.1 (2H); 7.4 (2H);
IR (KBr) ν cm$^{-1}$: 1750, 1710.

EXAMPLE 11

3-[4-[3-(2-methyl-1,3-dioxolane-2-yl)propyl]phenyl]-5(R)-methoxymethyl-2-oxazolidinone (code number 230084)

Method 1

To a solution of 1.83 g (6.28 mmol) of compound 230083 (Example 10) in 25 ml of toluene, is added 0.382 g (6.28 mmol) of ethylene glycol and the mixture is heated under reflux for 12 h in the presence of p-toluene sulphonic acid while removing the water. The reaction mixture is concentrated. The residue is taken up in $CH_2Cl_2$. The organic phase is washed with $NaHCO_3$, and then with water, dried and concentrated. The product is purified by HPLC (silica, eluent: isopropyl ether: 65; heptane: 25; methanol: 10).

m.p.=81° C.;
$[\alpha]_D^{20} = -49°(c=1, MeOH)$;
IR (KBr) $\nu$ cm$^{-1}$: 1740;
$^1$H NMR (CDCl$_3$) δ ppm: 1.25 (3H); 1.65 (4H); 2.55 (2H); 3.4 (3H); 3.6 (2H); 3.9 (6H); 4.65 (1H); 7.1 (2H); 7.4 (2H).

Method 2

Step 1

2,2-Dimethyl-4(S)-methoxymethyl-dioxolane (code number 370486)

To 910 ml of water, are added 910 g of NaOH as tablet, and then, at room temperature, 5 l of $CH_2Cl_2$, 44.4 g (0.195 mol) of benzyl triethylammonium chloride, 8,558.6 g (6.5 mol) of 2,2-dimethyl-3(S)-hydroxymethyldioxolane and 1,229.5 g (9.75 mol) of dimethyl sulphate. The reaction medium is stirred for 12 h and poured on water. The organic phase is concentrated. The product is distilled.

b.p.$_{10}$=45° C.
$[\alpha]_D^{20} = +7.9°(c=4, CH_3OH)$;
IR (microcell) $\nu$ cm$^{-1}$=2996, 2940, 2820, 1380, 1370, 840;
$^1$H NMR (CDCl$_3$) δ ppm =1.8 (3H); 1.4 (3H); 3.35 (3H);
3.4-4.4 (3H); 4 (2H). [J.A.C.S., 79, 1990 (1957)].

Step 2

3-Methoxy-propane-1,2-diol (R) (code number 370487)

A solution of 950.3 g (6.5 mol) of compound 370486 in 450 ml of water is heated at 60° C. and 3.2 ml of concentrated hydrochloric acid and then 9 ml of triethylamine are added, and the reaction medium is concentrated and distilled with a 84% yield.

b.p.$_1$=66° C.
$[\alpha]_D^{20} = -6.4°(c=4, CH_3OH)$;
IR (microcell) $\nu$ cm$^{-1}$: 3500-3300, 2960, 2945, 2910;
$^1$H NMR (DMSOd$_6$) δ ppm: 3.2-3.7 (8H); 4.5 (2 exch. H).

[J.A.C.S., 79, 1990 (1957)]

Step 3

3-Methoxy-propane-1,2-diol (S) tosylate (code number 370488)

A solution of 371.4 g (3.5 mol) of compound 370487 in 100 ml of toluene is cooled at 13° C. and 565 ml of pyridine and then gradually a solution of 700.6 g (3.675 mol) of paratoluene sulphonic chloride in 775 ml of toluene are added. The reaction medium is then stirred for 12 h and poured on water. The organic phase is washed with 2N hydrochloric acid and concentrated. The product is obtained with a 58% yield after chromatography (silica, eluent: $CH_2Cl_2$: 50; petroleum ether: 50). $[\alpha]_D^{20} = +5.3°(c=4, CH_3OH)$;
IR (microcell) $\nu$ cm$^{-1}$: 3500, 1335, 1185, 1170;
$^1$H NMR (CDCl$_3$) δ ppm: 2.4 (3H); 3.1 (1 exch. H); 3.2-3.6 (5H); 3.8-4.2 (3H).

Step 4

3-[4-[3-(2-methyl-1,3-dioxolane-2-yl)propyl]phenyl]-5(R)-methoxymethyl-2-oxazolidinone (code number 230084)

To 8.9 g (0.0887 mol) of phosgene in 120 ml of dichloroethane, are added 15.4 g (0.059 mol) of compound 370488, and then 13.3 g (0,0887 mol) of dimethylaniline dissolved in 20 ml of dichloroethane. The reaction medium is stirred for 1 h 30 at 50° C. After cooling, the latter is washed with iced water and dried over sodium sulphate. This solution is added to a solution of 13 g (0.059 mol) of compound 230113 (Example 9—Step 3) and 7.2 g (0.059 mol) of 4-dimethylaminopyridine in 200 ml of dichloroethane. The reaction medium is then heated under reflux for 30 min., cooled and poured on water. The organic phase is washed with a solution of sodium bicarbonate, dried and concentrated. The product is obtained after chromatography (silica, eluent: isopropyl ether: 65; heptane: 25; $CH_3OH$:10) with a 47% yield and has the same physical characteristics as those obtained by Method 1.

Method 3

Step 1

4-Methoxymethyl-1,3-dioxolane-2-one (S) (code number 360287)

A mixture of 14 g (0.132 mol) of compound 370487 (Method 2—Step 2), 31.16 g (0.264 mol) of diethyl carbonate in the presence of 0.108 g of 50% sodium hydride is heated until distillation of the alcohol formed. After completion of the reaction, the aimed product is distilled.

b.p.$_{0.3}$: 117° C.; Yield: 93%;
$[\alpha]_D^{20}: -32.2°(c=1, CH_2Cl_2)$;
IR (microcell) $\nu_{CO}$: 1790 cm$^{-1}$;
$^1$H NMR (CDCl$_3$) δ ppm: 3.4 (3H); 3.6 (2H); 4.3-4.9 (3H).

Step 2

2-[4-(ethoxycarbonylamino)phenylpropyl]-2-methyl-1,3-dioxolane (code number 360274)

To a solution of 6 g (0.027 mol) of compound 230113 (Example 9—Step 3) in a mixture of 63 ml of THF and 7 ml of water, are dropwise added at 25° C. 3.23 g (0.0405 mol) of $NaHCO_3$, and then dropwise 3.23 g (0.0298 mol) of ethyl chloroformate. After 1 h of stirring, the reaction medium is filtered and extracted with ethyl acetate. The organic phase is dried over $Na_2SO_4$ and concentrated. The product is obtained with a 57% yield after chromatography (Silica, Heptane: 80; Ethyl acetate: 20);

m.p.=65° C.
IR (KBr) $\nu_{co}$: 1700 cm$^{-1}$;
$^1$H NMR (CDCl$_3$) δ ppm: 1.1-1.4 (6H); 1.6-1.7 (4H); 2.4-2.7 (2H); 3.9-4.4 (6H);
6.8-7.4 (5H).

Step 3

3-[4-[3-(2-methyl-1,3-dioxolane-2-yl)propyl]phenyl]-5(R)-methoxymethyl-2-oxazolidinone (code number 230084)

1 g (3.4×10⁻³ mol) of compound 360274 and 0.6 g (4.3×10⁻³ mol) of compound 360287 (obtained at Steps 1 and 2) are mixed with 50 mg (0.34×10⁻³ mol) of $K_2CO_3$. The mixture is heated until $CO_2$ evolves (150° C.). After 30 min., the reaction medium is cooled and the product is obtained after chromatography (Silica, Heptane: 70, Ethyl acetate: 30) with a 100% yield. The product has the same characteristics as those obtained by Method 1.

In the same manner, there is obtained
3-[4-[3-(2-trifluoromethyl- 1,3-dioxolane-2-yl)-propyl]-phenyl]-5(R)-methoxymethyl-2-oxazolidinone.

Method 4

Step 1

1-bromo-3-methoxy-2-propanol benzoate (S) (code number 360065)

To a solution of 13.6 g (0.07 mol) of 2-phenyl 4-methoxymethyl 1,3-dioxolane (S) (Austr. J. Chem. 761, 29. 1976) in 40 ml of dichloroethane, are gradually added 12.5 g (0.07 mol) of N-bromosuccinimide while keeping temperature at 25° C. After 1 h of stirring, the reaction medium is poured on water. The organic phase is washed with a solution of sodium thiosulphate, and then with water, dried over magnesium sulphate and concentrated. The product is obtained with a 93% yield, after chromatography (Silica, Heptane: 60 Ethyl acetate: 40).

b.p.$_{0.5}$=95° C.;
IR (microcell) $\nu_{co}$:1720 cm⁻¹;
¹H NMR (CDCl₃) δ ppm: 3.4 (3H); 3.6–3.8 (4H); 5.3 (1H); 7.2–7.6 (3H); 7.9–8.1 (2H).

Step 2

3-[4-[3-(2-methyl-1,3-dioxolane-2-yl)propyl]phenyl]-5(R)-methoxymethyl-2-oxazolidinone (code number 230084)

To a suspension of 1.96 g (0.041 mol) of NaH (50% in oil) in 100 ml of THF, are added 5 g (0.017 mol) of compound 360274 (Method 3—Step 2), dissolved in 25 ml of THF. After 30 min. of stirring at 30° C.-40° C., are added 4.64 g (0.017 mol) of compound 360065 dissolved in 25 ml of THF and the reaction medium is heated at 50° C.-60° C. for 22 h. The reaction medium is cooled and poured on 500 ml of water. The aqueous phase is saturated with NaCl and extracted with ethyl acetate and then with methylene chloride. The organic phases are dried over $Na_2SO_4$ and concentrated. The residue is taken up in ethyl ether. After treatment by animal black, the ethereal solution is concentrated and the product is recrystallized from isopropanol alcool with a 30% yield. The obtained product has the same physical characteristics as those obtained by Method 1.

It should be noted that compound 230084 can also be obtained by hydrogenation under hydrogen pressure in the presence of 10% Pd/C in ethanol of compound 360392, the synthesis of which is described in Example 12 below.

EXAMPLE 12

3-[4-(2-methyl-1,3-dioxolane 2-yl-1-propenylene)-phenyl]-5(R)-methoxymethyl-2-oxazolidinone (code number 360392)

Step 1

4-(Terbutyl dimethyl silyloxy methyl)-1-nitro-benzene (code number 230245)

To a solution of 465 g (3.0339 mol) of paranitrobenzyl alcohol in 2.5 l of DMF, are added 310 g (4.559 mol) of imidazole, and then 504 g (3.347 mol) of terbutyl dimethylchlorosilane. After 1 h of stirring at room temperature, the reaction medium is poured on water. The aqueous phase is extracted with methylene chloride. The organic phase is dried over $Na_2SO_4$ and concentrated: oil;

¹H NMR (CDCl₃) δ ppm: 0.2 (6H); 1 (9H); 4.9 (2H); 7.6 (2H); 8.2 (2H);
IR (microcell) $\nu$ cm⁻¹: 1520, 1340, 1030, 840.

Step 2

4-(Terbutyl dimethyl silyloxy methyl-aniline (code number 230246)

To 772 ml of 0.1N ammonium chloride, are added 77.2 g (0.288 mol) of the previously obtained compound (230245) and 120.8 g of powdered iron and the mixture is heated under reflux for 2 h. After cooling, 20 ml of concentrated aqueous ammonia are added, the reaction medium is filtered and extracted with toluene. The organic phase is washed with water, dried over $Na_2SO_4$ and concentrated.

b.p.$_{0.01}$: 88°–93° C.;
¹H NMR (CDCl₃) δ ppm: 0.2 (6H); 1.05 (9H); 3.6 (2H);
IR (microcell) $\nu$ cm⁻¹: 3450, 3350.

Step 3

3-[4-(terbutyl dimethyl silyloxy methyl)phenyl]-5(R)-methoxymethyl-2-oxazolidinone (code number 230247)

To a solution of 43.8 g (0.168 mol) of compound 370488 (Example 11—Method 2—Step 3) in 200 ml of toluene, are added 130 ml of a 1.93 molar toluene solution of phosgene, and then dropwise 37.8 g (0.252 mol) of diethylaniline. After cooling, iced water is added and the organic phase is decanted and dried over $Na_2SO_4$. This solution is then added to a solution of 40 g (0.168 mol) of compound 230246 and of 20.5 g (0.168 mol) of 4-dimethylaminopyridine in 600 ml of toluene. After ½ h of stirring, the reaction medium is poured on water and the organic phase is washed with a solution of sodium bicarbonate, and then with a NaCl saturated solution. After concentration, the obtained product 84.5 g) is dissolved in 800 ml of ethanol to which are added 12.2 g (0.218 mol) of KOH as tablet. After ½ h of stirring, the reaction medium is poured in water and extracted with $CH_2Cl_2$. The organic phase is dried over $Na_2SO_4$ and concentrated. The aimed product is obtained after chromatography (silica, eluent: ethyl acetate 30, heptane 70) with a 63% yield.

$[\alpha]_D^{20}$ = −46.2°(c=1, $CH_3OH$);
IR (KBr) $\nu$ cm⁻¹: 1755, 1735;
¹H NMR (CDCl₃) δ ppm: 0 (6H); 1 (9H); 3.4 (3H); 3.6 (2H); 3.8–4.2 (2H); 4.7 (3H); 7.5 (4H);
m.p.<50° C.

Step 4

3-[4-(hydroxymethyl)phenyl]-5(R)-methoxymethyl-2-oxazolidinone (code number 230248)

A solution of 29.2 g (0.083 mol) of compound 230247 and 7.8 g (0.025 mol) of terbutylammonium fluoride trihydrate in 200 ml of THF is stirred for 12 h at room temperature and the reaction medium is concentrated. The product is obtained after chromatography (silica, eluent: ethyl acetate 50, heptane 50);

m.p.=65° C.;
IR (KBr) $\nu$ cm$^{-1}$: 3400, 1750, 1720,
$^1$H NMR (CDCl$_3$) $\delta$ ppm: 2.4 (1 exch. H); 3.35 (3H); 3.6 (2H); 3.8–4.2 (2H);
4.6 (2H); 7.35 (4H).

Step 5

3-(4-carboxyaldehydophenyl)-5 (R)-methoxymethyl-2-oxazolidinone (code number 230256)

To a solution cooled at $-60°$ C. of 12.46 g (0.0982 mol) of oxalyle chloride in 80 ml of CH$_2$Cl$_2$, is introduced over 20 min. a solution of 12.76 g (0.1630 mol) of DMSO in 80 ml of CH$_2$Cl$_2$. After 40 min. of stirring, a solution of 19.6 g (0.0818 mol) of compound 230248 in 80 ml of CH$_2$Cl$_2$ is added, and then 41.4 g (0.409 mol) of triethylamine. After return to room temperature, 300 ml of water are added. The organic phase is washed with water, dried and concentrated. The product was obtained after purification by chromatography (silica, eluent: ethyl acetate 70, heptane 30) with a 80% yield;

m.p.=96° C.;
$[\alpha]_D^{20} = -73,4°(c=1, CH_2Cl_2)$;
IR (KBr) $\nu$ cm$^{-1}$: 1740, 1690;
$^1$H NMR (CDCl$_3$) $\delta$ ppm: 3.4 (3H); 3.7 (2H); 3 8–4.3 (2H); 4.8 (1H);
7.8 (4H); 9.8 (1H).

Step 6

3-[4-(2-methyl-1,3-dioxolane-2-yl-1-propenylene)-phenyl]-5(R)-methoxymethyl-2-oxazolidinone (code number 360392)

A mixture of 0.470 g (2×10$^{-3}$ mol) of compound 230256, 0.4!4 g (3×10$^{-3}$ mol) of K$_2$CO$_3$, 1.14 g (2×5.10$^{-3}$ mol) of the phosphonium compound used in step 1 of example 9, dissolved in 2 ml of dioxane and 0.072 ml of water is heated at 80° C. for 3 h. The reaction medium is poured on water and extracted with ethyl acetate. The organic phase is dried and concentrated. The product is obtained after chromatography (silica, heptane: 40, ethyl acetate: 60), with a 31% yield.

$^1$H NMR (CDCl$_3$) $\delta$ ppm: 1.3 (3H); 2.6 (2H); 3.4 (3H); 3.6 (2H); 4 (6H): 4.7 (1H);
5.7 (1H); 6.4 (1H);
7.7–7.6 (4H).

EXAMPLE 13

3-[4-[3-(2-methyl-1,3-dioxolane-2-yl)propyl]phenyl]5-methoxymethyl-2-oxazolidinone (code number 230331)

Step 1

2-[3-[4-(2,3-dihydroxypropyl)aminophenyl]propyl]2-methyl-1,3-dioxolane (code number 230329)

To a solution of 10 g (0.045 mol) of compound 230113 (Example 9—Step 3) in 60 ml of ethanol, are added 3.34 g (0.045 mol) of glycidol and left under stirring overnight. After concentration, the product is obtained by chromatography (silica, eluent CH$_2$Cl$_2$: 97, CH$_3$OH: 3); Yield =44%.

Step 2

3-[4-[3-(2-methyl-1,3-dioxolane-2-yl)propyl]phenyl]-5-hydroxymethyl-2-oxazolidinone (code number 230330)

To a solution of 5.7 g (0.019 mol) of 230329 in 50 ml of toluene, are added 2.77 g (0.0023 mol) of diethyl carbonate at 97° C. and 1 ml of sodium ethoxide is gradually added. Then the mixture is heated at 110° C. while distillating off the alcohol. 1 h 30 later, the reaction medium is concentrated and taken up in water and extracted with chloroform. The organic phase is dried over Na$_2$SO$_4$ and concentrated. Yield =50%;

m.p.=72° C.;
IR (KBr) $\nu$ cm$^{-1}$: 3500, 1765.
$^1$H NMR (DMSOd$_6$) $\delta$ ppm: 1.2 (3H); 1.6 (4H); 2.5 (2H);
3.6 (2H); 3.8 (4H); 4 (2H);
4.6 (1H); 5.2 (1H); 7.2 (2H);
7.4 (2H).

Step 3

3-[4-[3-(2-methyl-1,3-dioxolane-2-yl)propyl]phenyl]-5-methoxymethyl-2-oxazolidinone (code number 230331)

This compound can be obtained by carrying out an identical procedure as that of Example 8.

m.p.=60° C.;
IR (KBr) $\nu$ cm$^{-1}$: 1735
$^1$H NMR (CDCl$_3$) $\delta$ ppm: 1.3 (3H); 1.6 (4H); 2.6 (2H); 3.4 (3H); 3.6 (2H); 3.9 (6H);
4.7 (1H); 7.2 (2H); 7.4 (2H).

EXAMPLE 14

N-ethoxycarbonyl 4-benzyloxy-aniline (code number 360343)

To a solution of 10 g (10$^{-3}$ mol) of benzyloxyaniline aniline in 90 ml of THF and 10 ml of water, are added 6.3 g of sodium bicarbonate, and then 5.28 g (55×10$^{-3}$ mol) of ethyl chloroformate. After 18 h of stirring, the reaction medium is filtered and concentrated. The residue is taken up in ethyl acetate. The organic solution is washed with water, dried over Na$_2$SO$_4$ and concentrated. The product is obtained with a 91% yield.

m.p.=98° C.;
IR (KBr) $\nu$ cm$^{-1}$: 3320, 1700, 1510–1530, 1230;
$^1$H NMR (CDCl$_3$) $\delta$ ppm: 1.2 (3H); 4.2 (2H); 5 (2H);
6.7 (1H); 6.9 (2H); 7.2 (2H).

EXAMPLE 15

3-(4-benZyloxyphenyl)-5(R)-methoxymethyl-2-oxazolidinone (code number 200404)

a) 1 g (3.6.10$^{-3}$ mol) of compound 360343 (Example 14), 0.099 g (0.72×10$^{-3}$ mol) of K$_2$CO$_3$ and 0.586 g (4.5×10$^{-3}$ mol) of compound 360287 (Example 11—Method 3—Step 1) are heated at 160° C. under stirring for 3 h. After cooling, the reaction medium is taken up in methylene chloride, washed with water, dried over Na$_2$SO$_4$, and concentrated. The product is recrystallized from isopropanol. Yield=71%. It has the same physical characteristics as those of compound of the Example 1.

b) A solution of 1 g (10$^{-3}$ mol) of benzyloxy-isocyanate, isocyanate, 0.56 g (4.4×10$^{-3}$ mol) of compound 360287, 28 mg of LiBr, 55mg of nBu$_3$PO (tributyl phosphine oxide) in 10 ml of toluene are heated under reflux for 18 h. After concentration, the precipitate is washed with water and isopropyl ether. Yield: 65%.

EXAMPLE 16

3-[4-[3-(2-phenylmethyl-1,3-dioxolane-2-yl)propyl]-phenyl]-5(R)-methoxymethyl-2-oxazolidinone (code number 360334)

Step 1

2-[2-(phenylmethyl)-1,3-dioxolane-2-yl]ethanol (code number 36037)

Obtained according to the method described in Example 7 (Step 1) from [2-(phenylmethyl)-1,3-dioxolane2-yl]acetic acid ethyl ester (Synthesis 451, 1982):

IR (microcell) $\nu$ cm$^{-1}$: 3440–3400;
$^1$H NMR (CDCl$_3$) $\delta$ ppm: 1.9 (2H); 2.8 (3H of which 1 exch.); 3.5–4 (6H);
7.2 (5H);

Step 2

2-(phenylmethyl)-2-(2-bromoethyl)-1,3-dioxolane (code number 360371)

To a solution of 37.8 g (0.181 mol) of compound 360370 in 200 ml of CH$_2$Cl$_2$, are added 120.4 g (0.363 mol) of CBr$_4$, and then gradually 95.2 g (0.363 mol) of triphenylphosphine, and then the reaction medium is stirred at room temperature for ½ hour. After filtration, the organic phase is concentrated. Yield: 81%;

IR (microcell) $\sigma$ cm$^{-1}$: 3020, 2960, 2880, 1605;
$^1$H NMR (CDCl$_3$) $\delta$ ppm: 2.2 (2H); 2.8 (2H); 3.4 (2H); 3.8 (4H); 7.2 (5H).

Step 3

[[2-(phenylmethyl)-1,3-dioxolane 2-yl]ethyl]-triphenylphosphonium bromide
(code number 360372)

To a solution of 33 g (0.1217 mol) of compound 360371 in 200 ml of dioxane, are added 31 g (0.1217 mol) of triphenylphosphine and the mixture is heated for 20 hours. After cooling, the precipitate is filtered and washed with dioxane and ethyl ether. Yield: 81%;
m.p. = 225° C.;
5 $^1$H NMR (CDCl$_3$) $\delta$ ppm: 1.6–2.2 (2H); 3 (2H); 3.2–4.2 (6H); 7.2 (5H); 1. 7.5–7.9 (15H).

In the same manner, there were obtained
[2-(2-phenyl-1,3-dioxolane-2-yl)ethyl]triphenylphosphonium bromide
[m.p.:228° C.
$^1$H NMR (CDCl$_3$) $\delta$ ppm: 2–2.5 (2H); 3.4–4.4 (6H); 7.4 (5H); 7.6–8 (15H)]from 2-phenyl-2-(2-bromoethyl)-1,3-dioxolane (Tetrahedron Letters, 1987 28, 1397).
[2-(2-cyclohexyl-1,3-dioxolane-2-yl)ethyl]triphenylphosphonium bromide from 2-cyclohexyl-2-(2-bromoethyl)-1,3-dioxolane: Liq.,
IR (microcell) $\nu$ cm$^{-1}$: 2920–2850, 1440–1110;
$^1$H NMR (CDCl$_3$) $\delta$ ppm: 0.9–2.3 (13H); 3–4.2 (6H); 7.6–8 (15H).

Step 4

2-(Para-nitrocinnamyl)-2-(phenylmethyl)-1,3-dioxolane (code number 360373)

Obtained according to the procedure of Step 1 of Example 9: liquid;
IR (microcell) $\nu$ cm$^{-1}$: 1595, 1510, 1340,
$^1$H NMR (CDCl$_3$) $\delta$ ppm: 2.6 (2H); 3 (2H); 3.9 (4H); 5.8–6.8 (2H); 7.3 (5H);
7.4 (2H); 8.2 (2H).

In the same manner, there were obtained:
2-(para-nitrocinnamyl)-2-phenyl-1,3-dioxolane (code number 360384)
IR (microcell) $\nu$ cm$^{-1}$: 1595, 1510, 1340,
$^1$H NMR (CDCl$_3$) $\delta$ ppm: 2.8–3 (2H); 3.6–4.2 (4H); 5.6–6.8 (2H);
7.15–7.65 (7H); 8.1 (2H);
m.p. = 82° C.;
2-(para-nitrocinnamyl)-2-cyclohexyl-1,3-dioxolane (code number 360416)
IR (microcell) $\nu$ cm$^{-1}$: 2920–2850, 1595–1510, 1390,
$^1$H NMR (CDCl$_3$) $\delta$ ppm: 0.8–2.1 (11H); 2.5–2.8 (2H); 4 (4H);
5.7–6.7 (2H); 7.45 (3H);
8 2 (2H).

Step 5

2-[3-(4-aminophenyl)propyl]-2-(phenylmethyl)-1,3-dioxolane (code number 360374)

To a solution of 21.7 g (0.066 mol) of compound 360373 in 250 ml of THF, are added 4 g of 10% Pd/C, a hydrogen stream is passed through under normal pressure while keeping temperature at 50–60° C. After completion of the reaction, the reaction medium is filtered and concentrated and the product is obtained after purification by chromatography (silica; eluent: heptane 70; ethyl acetate: 30); Yield = 71%;
m.p. = 55° C.;
IR (KBr) $\nu$ cm$^{-1}$: 3450–3360, 1620–1510;
$^1$H NMR (CDCl$_3$) $\delta$ ppm: 1.65 (4H); 2.45 (2H); 2.85 (2H); 3.45 (2 exch. H);
3.45–4 (4H); 6.5 (2H);
6.9 (2H); 7.2 (5H).

In the same manner, there were obtained:
2-[3-(4-aminophenyl)propyl]-2-phenyl-1,3-dioxolane (code number 360385)
m.p. = 68° C.;
IR = (KBr) $\nu$ cm$^{-1}$: 3440–3360, 1630–1610, 1515;
$^1$H NMR (CDCl$_3$) $\delta$ ppm: 1.4–2.2 (4H); 2.4 (2H); 3.45 (2H); 3.6–4.15 (4H);
6.5 (2H); 6.9 (2H);
7.2–7.6 (5H);
2[3-(4-aminophenyl)propyl]-2-cyclohexyl-3-dioxolane (code number 360417)
IR (microcell) $\nu$ cm$^{-1}$: 3440–3360, 1625;
$^1$H NMR (CDCl$_3$) $\delta$ ppm: 0.8–2 (11H); 2.4 (2H); 3 45 (2 exch. H); 3.8 (4H);
6.5 (2H); 6.9 (2H).

Step 6

2-[3-[4-(ethoxycarbonylamino)phenyl]propyl]-2-(phenylmethyl)-1,3-dioxolane (code number 360375)

Obtained according to the procedure of Step 2 of Method 3 of Example 11.
$^1$H NMR (CDCl$_3$) $\delta$ ppm: 1.25 (3H); 1.65 (4H); 2.5 (2H); 2.85 (2H); 3.7 (4H);
4.2 (2H); 6.9 (1 exch. H);
7–7.4 (9H).

In the same manner, there were obtained:
2-[3-[4-(ethoxycarbonylamino)phenyl]propyl]-2-phenyl-3-dioxolane (code number 360386)
$^1$H NMR (CDCl$_3$) $\delta$ ppm: 1.25 (3H); 1.4–2.2 (4H); 2.5 (2H); 3.5–4 (4H);
4.2 (2H); 6.6–7.6 (10H of which 1 exch.);
m.p. = 66° C.
2-[3-[4-(ethoxycarbonylamino)phenyl]propyl]-2-cyclohexyl-1,3-dioxolane (code number 360420)
m.p. = 70° C.
IR (KBr) $\nu$ cm$^{-1}$: 3360, 1705.

Step 7

3-[4-[3-(2-phenylmethyl-1,3-dioxolane-2-yl)propyl]-phenyl]-5(R)-methoxymethyl-2-oxazolidinone (code number 360334)

Obtained according to the procedure of Example 11 (Method 3, Step 3).

$^1$H NMR (CDCl$_3$) δ ppm: 1.6 (4H); 2.5 (2H); 2.85 (2H);
3.4 (3H); 3.45–4.2 (8H);
4.65 (1H); 6.9–7.6 (9H).
$[α]_D^{20}$: −33.2°(c=1, CH$_2$Cl$_2$)

In the same manner, there were obtained:

3-[4-[3-(2-phenyl-1,3-dioxolane-2-yl)propyl]phenyl]-5(R)-methoxymethyl-2-oxazolidinone (code number 360332)

$^1$H NMR (CDCl$_3$) δ ppm: 1.4–2.1 (4H); 2.55 (2H); 3.4 (3H); 3.6 (2H);
3.6–4.2 (6H); 4.65 (1H);
6.95–7.95 (9H);
IR (KBr) ν cm$^{-1}$: 1750;
$[α]_D^{20}$ = −31.9°(c=1, CH$_2$Cl$_2$)

3-[4-[3-(2-cyclohexyl-1,3-dioxolane-2-yl)propyl]-phenyl]-5(R)-methoxymethyl-2-oxazolidinone (code number 360354)
m.p. = 86° C.

EXAMPLE 17

3-[4-[2-(2-trifluoromethyl-1,3-dioxolane-2-yl)-ethoxy]-phenyl]-5(R)-methoxymethyl-2-oxazolidinone (code number 360396)

Step 1

[2-(trifluoromethyl)-1,3-dioxolane-2-yl]ethanol (code number 360405)

Was obtained according to the procedure of Example 7 (Step 1) by reducing the 2-trifluoromethyl-1,3-dioxolane-2-yl acetic acid ethyl ester (J. Fluorine. Chem. 44, 377, 1989).

IR (microcell) ν cm$^{-1}$: 3350–3400, 1170–1070, 1035;
$^1$H NMR (CDCl$_3$) δ cm$^{-1}$: 2.5 (3H of which 1 exch.); 3.8 (2H); 4.2 (4H).

In the same manner, there was obtained
[2-(pentafluoroethyl)-1,3-dioxolane-2-yl]ethanol.

Step 2

[2-(trifluoromethyl)-1,3-dioxolane-2-yl]ethanol mesylate (code number 360406)

To a solution of 20 g.(0.107 mol) of compound 360405 in 200 ml of CH$_2$Cl$_2$, are added 12.9 g (0.128 mol) of triethylamine, and then at 0° C., dropwise, 14.8 g (0.128 mol) of mesyl chloride. The reaction medium is stirred at room temperature up to disappearance of the starting materials. It is then poured on water, the organic phase is washed with water, dried over Na$_2$SO$_4$ and concentrated. The product is obtained with a 100% yield.

IR (microcell) ν cm$^{-1}$: 1350–1170;
$^1$H NMR (CDCl$_3$) δ ppm: 2.35 (2H); 3 (3H); 4.2 (4H); 4.4 (2H).

Step 3

3-[4-[2-(2-trifluoromethyl-1,3-dioxolane-2-yl)-ethoxy]-phenyl]-5(R)-methoxymethyl-2-oxazolidinone (code number 360396)

To a solution of 23.65 g (0.105 mol) of compound 200405 (Example 2) in 200 ml of acetonitrile and 20 ml of DMF, are added 29 g (0.21 mol) of K$_2$CO$_3$, and then 28 g (0.105 mol) of compound 360406 and the resulting solution is heated under reflux overnight. After cooling, the reaction medium is filtered and poured on ethyl acetate. The organic solution is washed with N sodium hydroxide and with water, dried over Na$_2$SO$_4$ and concentrated. The product is obtained after chromatography (silica, eluent: CH$_2$Cl$_2$: 99; acetone: 1). Yield: 60%; m.p. = 112° C.;

$^1$H NMR δ ppm: 2.25 (2H); 3.4 (3H); 3.6 (2H);
3.75–4.3 (8H); 4.7 (1H); 6.85 (2H);
7.4 (2H).

In the same manner compounds 370506, 370445, 230046 and 230204 mentioned in Example 3 were obtained.

EXAMPLE 18

2-cyclohexyl-2-(2-bromoethyl)-1,3-dioxolane (code number 360414)

Step 1

3-bromo-1-cyclohexyl-propanone

In a solution of 1-cyclohexyl-1-one-2-propene (0.255 mol) in 200 ml of CH$_2$Cl$_2$, cooled at 10–15° C., HBr gas is bubbled through. After completion of the reaction, the reaction medium is washed with an aqueous NaHCO$_3$ saturated solution, dried over Na$_2$SO$_4$ and concentrated to obtain the aimed product as an oil.

Step 2

2-cyclohexyl-2-(2-bromoethyl)-1,3 dioxolane

A solution of the compound obtained in the previous step (0.223 mol) in 600 ml of benzene, this solution further comprising 0.58 mol of ethylene glycol and 2.5 g of paratoluene sulphonic acid is refluxed while removing the formed water. After 3 hours 30 min. of reaction, the solution is poured in a saturated NaCl solution, the organic phase is dried over Na$_2$SO$_4$, concentrated and purified by chromatography (silica, eluent: heptane 60—CH$_2$Cl$_2$ 40).

The derivatives of formula (I), including the racemates for which R$_1$=CH$_3$; X=oxygen; n=1 or 2; R$_2$=R$'_2$=H; R$_3$=CH$_3$; and R$_4$ and R$'_4$ form together a —(CH$_2$)$_2$— chain, as well as the physiologically acceptable salts thereof when they exist have been studied on experimental animals and showed pharmacological activities, particularly in the psychotropic field, specially as anxiolytics and potential antidepressants.

The antidepressive activity is demonstrated by the 5-HTP potentialisation assay in rat according to the procedure described by: M. Jalfre, B. Bucher, A. Coston, G. Mocquet and R.D. Porsolt: Arch. Int. Pharmacodyn. (1982), 259, 194–221: the dose of product which, when given orally, brings about in 50% of the animals (ED$_{50}$) the appearance of generalized shakings or of stereotypies (trinklings, shakes of head) consecutive to the administration by intraperitoneal route 1 h after the first treatment of a dose of 120 mg of 5-hydroxy-tryptophane (5-HTP) is determined in rat.

The results obtained with some compounds according to the invention in the previously mentioned assay are set forth, by way of example, in the table below, in which is also mentioned the acute toxicity (LD$_{50}$) of some of the tested compounds and which is evaluated in mouse according to the method of J.T. Litchfield and F. Wilcoxon (J. Pharmacol. Exp. Ther. (1949), 96, 99).

TABLE

| Tested compound Code number | ED$_{50}$ mg/kg | LD$_{50}$ mg/kg p.o. |
| --- | --- | --- |
| 370296 | 0.87 | 1 000–1 200 |
| 370297 | 1.2 | 1 200 |
| 230084 | 0.97 | |
| TOLOXATONE | 30 | |

The previously mentioned results show that the compounds which make the subject-matter of the present invention can be used for the preparation of psychotropic drugs and particular anxiolytics and potential antidepressants, these drugs finding their use in therapy particularly for the treatment of endogenous and exogenous depressive states.

These drugs can be administred to humans or any warm-blooded animals in a variety of pharmaceutical forms well-known in the art and particularly in the form of compositions formulated for an administration by an oral, injectable or rectal route.

For the orally administration, said compositions can take the form of tablets, dragees or capsules prepared by the conventional techniques using known carriers and excipients, such as binding agents, fillers, lubricants and desintegration agents; they can also be in the form of solutions, syrups or suspensions.

For the administration in the form of an injectable solute, the compositions according to the invention may be in the form of injectable solutions, suspensions or emulsions containing an acceptable oily or aqueous liquid carrier.

For the rectal administration, the compositions may be in the form of suppositories containing the conventional bases for suppositories.

The therapeutic active dose of the active principles depends particularly on the administration route, the patient's body weight and on the therapeutic potency of the used active principles.

By oral route, the given doses may generally reach 10 mg/kg/day of active principle (in one or more intakes); by injectable route, they may reach 1 mg/kg/day (in one or more intakes); by rectal route, they may reach 5 mg/kg/day of active compound (in one or more suppositories).

We claim:

1. The derivatives of the formula:

$$R_3-\underset{\underset{R_4}{|}}{\underset{O}{\diagup}}C\underset{\underset{R'_4}{|}}{\underset{O}{\diagdown}}\overset{R'_2}{\underset{R_2}{|}}C-(CH_2)_n-X-\underset{}{\bigcirc}-N\underset{}{\diagup}\underset{\underset{O}{\parallel}}{\diagdown}O-OR_1 \quad (I)$$

where:
- $R_1$ is H or $C_1$-$C_4$ alkyl;
- X is an oxygen atom, a methylene group or a —CH=CH— group;
- n is 1 or 2 when X is an oxygen atom or a methylene group and is 0 or 1 when X is a —CH=CH— group;
- $R_3$ is a $C_1$-$C_4$ alkyl, $C_3$-$C_7$ cycloalkyl, phenyl, benzyl, $CHF_2$, $CF_3$ or $CF_3CF_2$ group;
- each of $R_2$ and $R'_2$ independently is a hydrogen atom or a $C_1$-$C_4$ alkyl, $C_4$-$C_7$ cycloalky, phenyl or benzyl group;
- $R'_2$ and $R_3$ may further form together a —(CH$_2$)$_3$— or —(CH$_2$)$_4$— chain; and
- each of $R_4$ and $R'_4$ independently is a $C_1$-$C_4$ alkyl group or $R_4$ and $R'_4$ form together either a —(CH$_2$)$_2$— or —(CH$_2$)$_3$— chain, a —(CH$_2$)$_2$— or —(CH$_2$)$_3$— chain substituted by one or two $C_1$-$C_4$ alkyl groups, or a —(CH$_2$)$_2$— chain substituted by one or two —CH$_2$—NH$_2$ groups or by one or two —CH$_2$—NH$_2$ groups N-substituted by one or two $C_1$-$C_4$ alkyl groups, these derivatives being under the form of diastereoisomers or enantiomers or under the cis- or trans-form or under the form of a mixture of all theses forms, including the racemic forms, with the exclusion of the racemates wherein $R_1=CH_3$ and the $$R_3-\underset{\underset{R_4}{|}}{\underset{O}{\diagup}}C\underset{\underset{R'_4}{|}}{\underset{O}{\diagdown}}\overset{R'_2}{\underset{R_2}{|}}C-(CH_2)_n-X-$$

chaining has the meaning:

$$CH_3-\underset{O}{\diagup}C\underset{O}{\diagdown}-(CH_2)_2-O \quad \text{or} \quad CH_3-\underset{O}{\diagup}C\underset{O}{\diagdown}-(CH_2)_3-O,$$

and the optional acid addition salts of said derivatives.

2. The derivatives and salts according to claim 1, wherein:
- $R_1=$H or CH$_3$;
- X=oxygen or CH$_2$;
- n=1 or 2;
- $R_2=R'_2=$H;
- $R_3=C_1$-$C_4$ alkyl; and
- $R_4$ and $R'_4$ are $C_1$-$C_4$ alkyl or form together a —(CH$_2$)$_2$—chain, a —(CH$_2$)$_2$— chain substituted by two dimethylaminomethyl groups, a —(CH$_2$)$_3$— chain or a —(CH$_2$)$_3$— chain substituted by two CH$_3$ groups.

3. The derivatives according to claim 1, wherein:
- $R_1=$CH$_3$;
- X=oxygen;
- n=1 or 2;
- $R_2=R'_2=$H;
- $R_3=$CH$_3$ or CF$_3$; and
- $R_4$ and $R'_4$ are CH$_3$ or form together a —(CH$_2$)$_2$— chain.

4. The derivatives according to claim 1, wherein:
- $R_1=$CH$_3$;
- X=methylene;
- n=1 or 2;
- $R_2=R'_2=$H;
- $R_3=$CH$_3$ or CF$_3$; and
- $R_4$ and $R'_4$ are CH$_3$ or form together a —(CH$_2$)$_2$— chain.

5. The derivatives according to claim 1, wherein $R_1=$CH$_3$; X is CH=CH; n=0 or 1; $R_2=R'_2=$H; $R_3=$CH$_3$ or CF$_3$ and $R_4$ and $R'_4$ are CH$_3$ or form together a —(CH$_2$)$_2$— chain.

6. The derivative according to claim 1, wherein:
- $R_1=$CH$_3$;
- X=methylene;
- n=1;
- $R_2=R'_2=$H;

$R_3 = CH_3$; and $R_4$ and $R'_4$ form together a $-(CH_2)_2-$ chain.

7. The derivative according to claim 6, wherein the asymmetric carbon atom has the (R) configuration.

8. A pharmaceutical composition, characterized in that it contains a physiologically acceptable excipient and a compound selected among those according to any one of claims 1 to 7 and the racemic derivatives of formula:

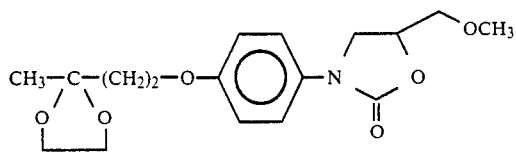

or

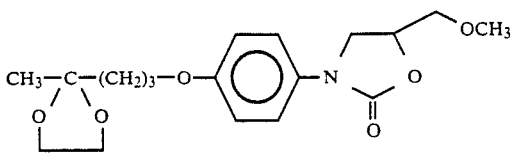

including the acid addition salts of these racemic derivatives.

9. The method of use of the compounds according to any one of claims 1 to 7 and of the racemic derivatives of formula:

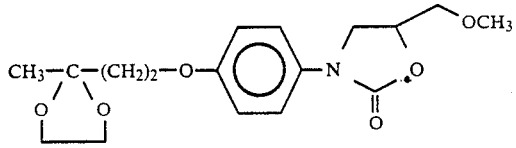

or

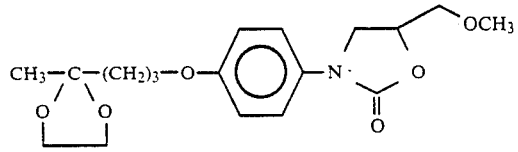

including the acid addition salts of these racemic derivatives in the treatment and therapy of depressive states.

* * * * *